United States Patent
Tsuda et al.

(10) Patent No.: US 11,111,526 B2
(45) Date of Patent: Sep. 7, 2021

(54) BUFFER COMPOSITION FOR HYBRIDIZATION AND HYBRIDIZATION METHOD

(71) Applicants: TOYO KOHAN CO., LTD., Tokyo (JP); YAMAGUCHI UNIVERSITY, Yamaguchi (JP)

(72) Inventors: Toshiya Tsuda, Yamaguchi (JP); Shuichi Kamei, Yamaguchi (JP); Mitsuyoshi Oba, Yamaguchi (JP); Hirofumi Yamano, Yamaguchi (JP); Ryouichi Tsunedomi, Yamaguchi (JP); Shoichi Hazama, Yamaguchi (JP); Hiroaki Nagano, Yamaguchi (JP)

(73) Assignees: Toyo Kohan Co., Ltd., Tokyo (JP); Yamaguchi University, Yamaguchi (JP)

( * ) Notice: Subject to any disclaimer, the term of this patent is extended or adjusted under 35 U.S.C. 154(b) by 81 days.

(21) Appl. No.: 16/322,363

(22) PCT Filed: Aug. 2, 2017

(86) PCT No.: PCT/JP2017/028141
§ 371 (c)(1),
(2) Date: Jan. 31, 2019

(87) PCT Pub. No.: WO2018/025938
PCT Pub. Date: Feb. 8, 2018

(65) Prior Publication Data
US 2019/0161791 A1    May 30, 2019

(30) Foreign Application Priority Data
Aug. 3, 2016    (JP) .............................. JP2016-153058

(51) Int. Cl.
| | | |
|---|---|---|
| *C12Q 1/68* | (2018.01) | |
| *C12Q 1/6832* | (2018.01) | |
| *C07H 21/00* | (2006.01) | |
| *C12N 15/09* | (2006.01) | |
| *C12M 1/00* | (2006.01) | |

(52) U.S. Cl.
CPC .......... *C12Q 1/6832* (2013.01); *C12N 15/09* (2013.01); *C12Q 1/68* (2013.01); *C12M 1/00* (2013.01)

(58) Field of Classification Search
CPC ......... C12Q 1/68; C12Q 1/6832; C07H 21/00
See application file for complete search history.

(56) References Cited

U.S. PATENT DOCUMENTS

| | | | |
|---|---|---|---|
| 7,439,016 B1 | 10/2008 | Anthony et al. | |
| 10,450,601 B2 * | 10/2019 | Kamei | ...................... C12Q 1/68 |
| 2006/0172333 A1 | 8/2006 | Chen et al. | |
| 2006/0211022 A1 | 9/2006 | Jing et al. | |
| 2015/0203905 A1 * | 7/2015 | Takahashi | ............ C12Q 1/6834 |
| | | | 435/6.11 |
| 2016/0265037 A1 * | 9/2016 | Kamei | ................... C12N 15/09 |

FOREIGN PATENT DOCUMENTS

| | | | | |
|---|---|---|---|---|
| EP | 1580269 A1 * | 9/2005 | ............. | C12N 15/09 |
| JP | 2004-511220 A | 4/2004 | | |
| JP | 2005-502346 A | 1/2005 | | |
| JP | 2010-200701 A | 9/2010 | | |
| WO | WO 03/020902 A2 | 3/2003 | | |
| WO | WO 2015/045741 A1 | 4/2015 | | |

OTHER PUBLICATIONS

International Search Report dated Oct. 31, 2017, in PCT/JP2017/028141.
Hiratsuka et al., "Genotyping of Single Nucleotide Polymorphisms (SNPs) Influencing Drug Response by Competitive Allele-specific Short Oligonucleotide Hybridization (CASSOH) with Irnmunochromatographic Strip," Drug Metab. Pharmacokin., 2004, 19(4):303-307.
Hiratsuka et al., "Competitive allele-specific short oligonucleotide hybridization (CASSOH) with enzyme-linked immunosorbent assay (ELISA) for the detection of pharmacogenetic single nucleotide polymorphisms (SNPs)," J. Biochem. Biophys. Methods, 2006, 67:87-94.
Supplementary European Search Report dated Feb. 24, 2020, in EP 17837040.9.
Fiandaca et al., "PNA Blocker Probes Enhance Specificity in Probe Assays, Peptide Nucleic Acids: Protocols and Applications," Jan. 1, 1999, 129-141.

* cited by examiner

*Primary Examiner* — Ethan C Whisenant
(74) *Attorney, Agent, or Firm* — Foley & Lardner LLP

(57) ABSTRACT

In the case of using a blocking nucleic acid to prevent non-specific hybridization of a target nucleic acid with a nucleic acid probe, further excellent efficiency of detecting the target nucleic acid is achieved. A buffer composition used in hybridization of a target nucleic acid with a nucleic acid probe, wherein the buffer composition for hybridization contains a blocking nucleic acid comprising a nucleotide sequence complementary to a region comprising at least a non-detection target nucleotide in a non-target nucleic acid, in a concentration of one or more times higher than the concentration of a nucleic acid in a nucleic acid mixture consisting of the target nucleic acid and the non-target nucleic acid.

3 Claims, 7 Drawing Sheets

Specification includes a Sequence Listing.

[Fig. 1-1]
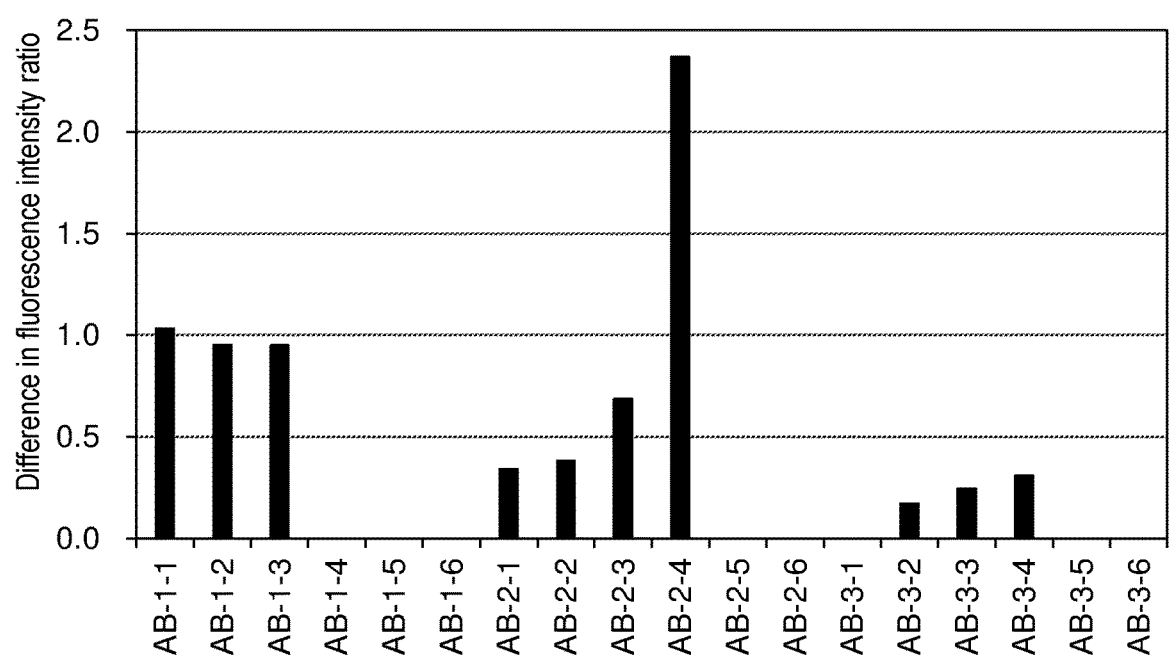

[Fig. 1-2]
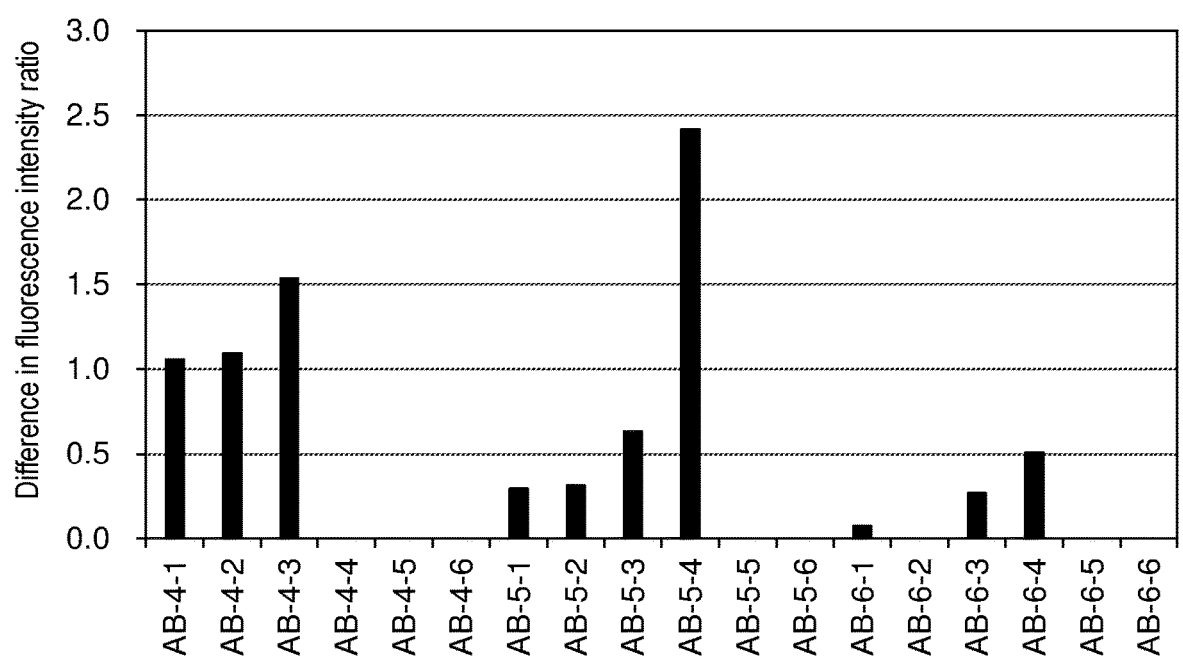

[Fig. 2-1]
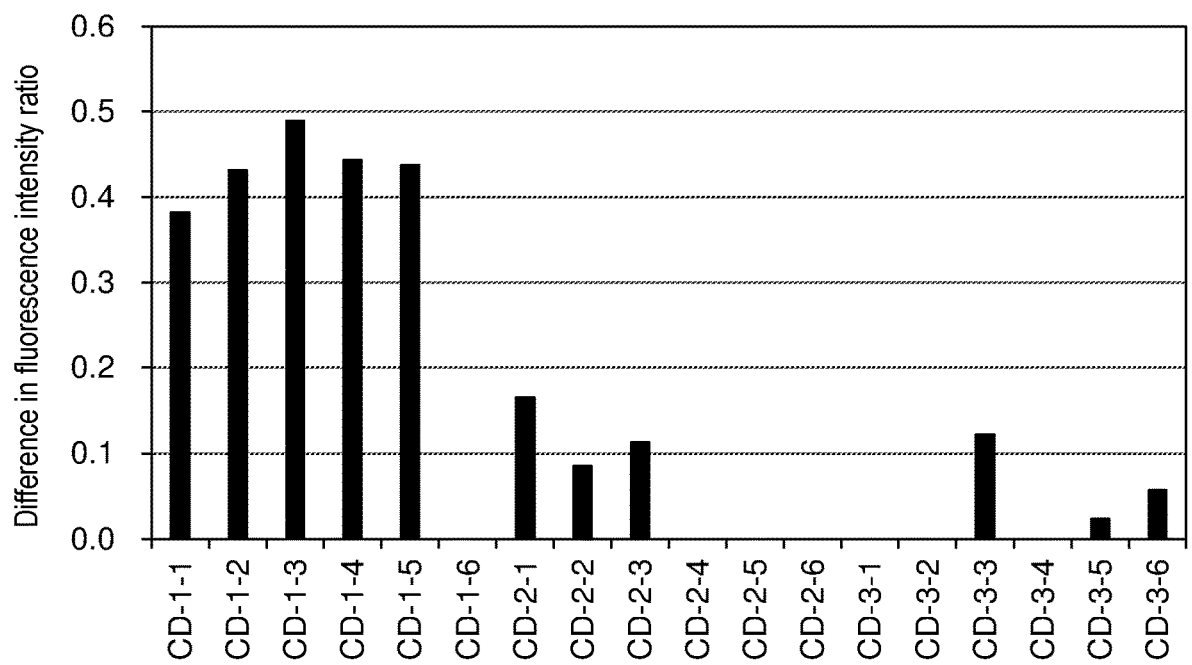

[Fig. 2-2]
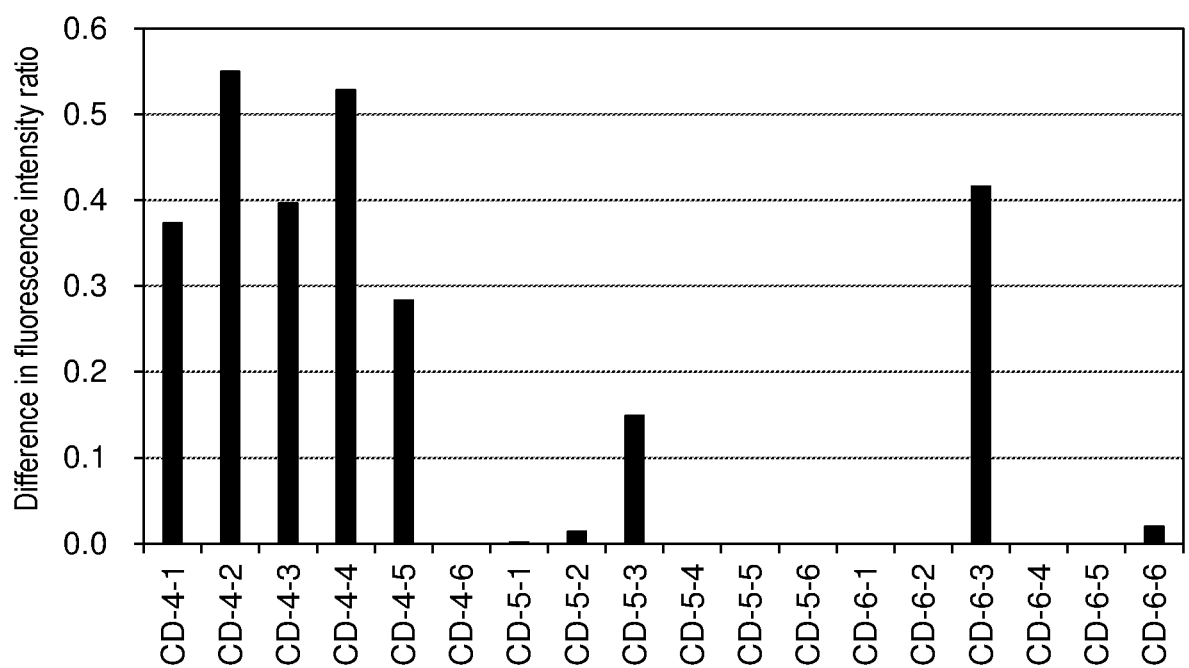

[Fig. 3-1]
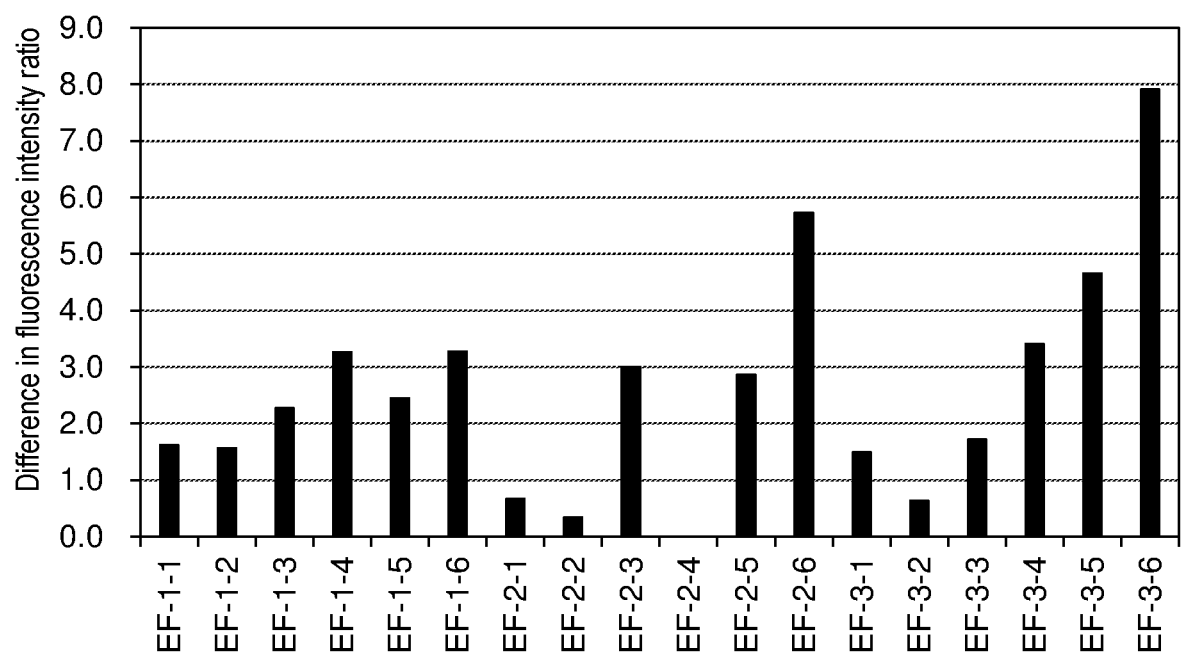

[Fig. 3-2]
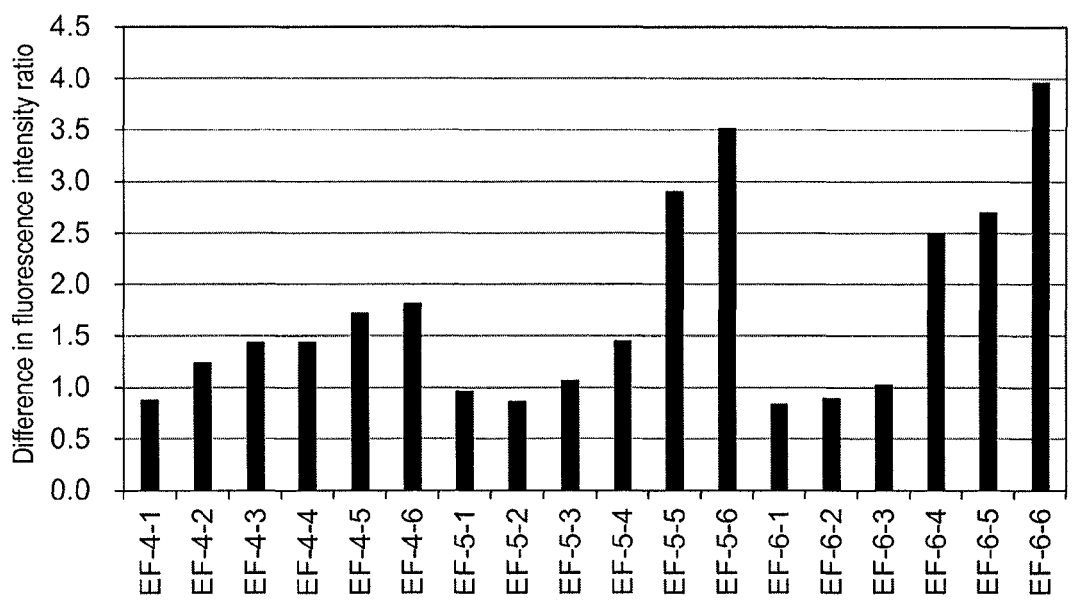

[Fig. 3-3]
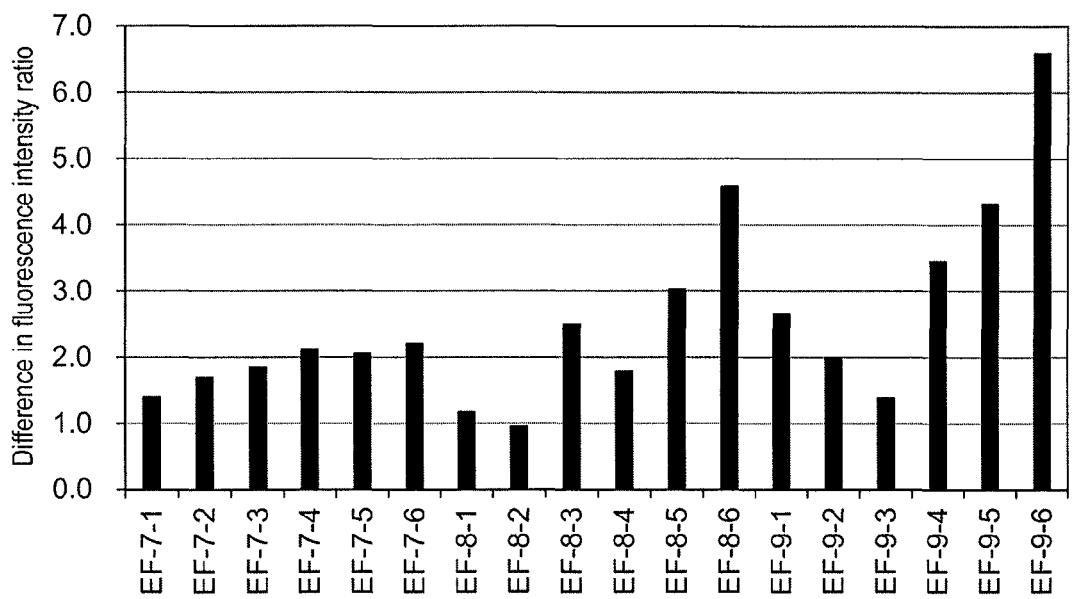

SEQUENCE LISTING

<160> NUMBER OF SEQ ID NOS: 20

<210> SEQ ID NO 1
<211> LENGTH: 36
<212> TYPE: DNA
<213> ORGANISM: Artificial

```
<220> FEATURE:
<223> OTHER INFORMATION: synthetic DNA

<400> SEQUENCE: 1
tatggtccta gtaggaaata aatgtgattt gccttc                                36

<210> SEQ ID NO 2
<211> LENGTH: 36
<212> TYPE: DNA
<213> ORGANISM: Artificial
<220> FEATURE:
<223> OTHER INFORMATION: synthetic DNA

<400> SEQUENCE: 2
tatggtccta gtaggaaata actgtgattt gccttc                                36

<210> SEQ ID NO 3
<211> LENGTH: 36
<212> TYPE: DNA
<213> ORGANISM: Artificial
<220> FEATURE:
<223> OTHER INFORMATION: synthetic DNA

<400> SEQUENCE: 3
tatggtccta gtaggaaata attgtgattt gccttc                                36

<210> SEQ ID NO 4
<211> LENGTH: 21
<212> TYPE: DNA
<213> ORGANISM: Artificial
<220> FEATURE:
<223> OTHER INFORMATION: synthetic DNA

<400> SEQUENCE: 4
gcaaatcaca tttatttcct a                                                21

<210> SEQ ID NO 5
<211> LENGTH: 21
<212> TYPE: DNA
<213> ORGANISM: Artificial
<220> FEATURE:
<223> OTHER INFORMATION: synthetic DNA

<400> SEQUENCE: 5
gcaaatcaca tttatttcct a                                                21

<210> SEQ ID NO 6
<211> LENGTH: 19
<212> TYPE: DNA
<213> ORGANISM: Artificial
<220> FEATURE:
<223> OTHER INFORMATION: synthetic DNA

<400> SEQUENCE: 6
caaatcacag ttatttcct                                                   19

<210> SEQ ID NO 7
<211> LENGTH: 21
<212> TYPE: DNA
<213> ORGANISM: Artificial
<220> FEATURE:
<223> OTHER INFORMATION: synthetic DNA

<400> SEQUENCE: 7
gcaaatcaca attatttcct a                                                21
```

<210> SEQ ID NO 8
<211> LENGTH: 26
<212> TYPE: DNA
<213> ORGANISM: Artificial
<220> FEATURE:
<223> OTHER INFORMATION: synthetic DNA

<400> SEQUENCE: 8
cttgcctacg ccaccagctc aacta                                         26

<210> SEQ ID NO 9
<211> LENGTH: 24
<212> TYPE: DNA
<213> ORGANISM: Artificial
<220> FEATURE:
<223> OTHER INFORMATION: synthetic DNA

<400> SEQUENCE: 9
cttgcctacg ccatcagctc caac                                          24

<210> SEQ ID NO 10
<211> LENGTH: 24
<212> TYPE: DNA
<213> ORGANISM: Artificial
<220> FEATURE:
<223> OTHER INFORMATION: synthetic DNA

<400> SEQUENCE: 10
cttgcctacg ccaacagctc caac                                          24

<210> SEQ ID NO 11
<211> LENGTH: 24
<212> TYPE: DNA
<213> ORGANISM: Artificial
<220> FEATURE:
<223> OTHER INFORMATION: synthetic DNA

<400> SEQUENCE: 11
cttgcctacg ccagcagctc caac                                          24

<210> SEQ ID NO 12
<211> LENGTH: 14
<212> TYPE: DNA
<213> ORGANISM: Artificial
<220> FEATURE:
<223> OTHER INFORMATION: synthetic DNA

<400> SEQUENCE: 12
gagctggtgg cgta                                                     14

<210> SEQ ID NO 13
<211> LENGTH: 14
<212> TYPE: DNA
<213> ORGANISM: Artificial
<220> FEATURE:
<223> OTHER INFORMATION: synthetic DNA

<400> SEQUENCE: 13
gagctggtgg cgta                                                     14

<210> SEQ ID NO 14
<211> LENGTH: 15
<212> TYPE: DNA
<213> ORGANISM: Artificial
<220> FEATURE:
<223> OTHER INFORMATION: synthetic DNA

```
<400> SEQUENCE: 14
gagctgatgg cgtag                                                      15

<210> SEQ ID NO 15
<211> LENGTH: 14
<212> TYPE: DNA
<213> ORGANISM: Artificial
<220> FEATURE:
<223> OTHER INFORMATION: synthetic DNA

<400> SEQUENCE: 15
agctgttggc gtag                                                       14

<210> SEQ ID NO 16
<211> LENGTH: 13
<212> TYPE: DNA
<213> ORGANISM: Artificial
<220> FEATURE:
<223> OTHER INFORMATION: synthetic DNA

<400> SEQUENCE: 16
gctgctggcg tag                                                        13

<210> SEQ ID NO 17
<211> LENGTH: 25
<212> TYPE: DNA
<213> ORGANISM: Artificial
<220> FEATURE:
<223> OTHER INFORMATION: synthetic DNA

<400> SEQUENCE: 17
gtgtgacatg ttctaatata gtcac                                           25

<210> SEQ ID NO 18
<211> LENGTH: 20
<212> TYPE: DNA
<213> ORGANISM: Artificial
<220> FEATURE:
<223> OTHER INFORMATION: synthetic DNA

<400> SEQUENCE: 18
gaatggtcct gcaccagtaa                                                 20

<210> SEQ ID NO 19
<211> LENGTH: 22
<212> TYPE: DNA
<213> ORGANISM: Artificial
<220> FEATURE:
<223> OTHER INFORMATION: synthetic DNA

<400> SEQUENCE: 19
ctctgaagat gtacctatgg tc                                              22

<210> SEQ ID NO 20
<211> LENGTH: 23
<212> TYPE: DNA
<213> ORGANISM: Artificial
<220> FEATURE:
<223> OTHER INFORMATION: synthetic DNA

<400> SEQUENCE: 20
gtctactgtt ctagaaggca aat                                             23
```

BUFFER COMPOSITION FOR HYBRIDIZATION AND HYBRIDIZATION METHOD

CROSS-REFERENCE TO RELATED APPLICATIONS

This application is the U.S. National Stage of PCT/JP2017/028141, filed Aug. 2, 2017, which claims priority to JP 2016-153058, filed Aug. 3, 2016.

The instant application contains a Sequence Listing which has been submitted in ASCII format via EFS-WEB and is hereby incorporated by reference in its entirety. Said ASCII copy, created on Jan. 30, 2019, is named sequence.txt and is 4 KB.

TECHNICAL FIELD

The present invention relates to a buffer composition for hybridization, which comprises a blocking nucleic acid having a nucleotide sequence complementary to a region comprising at least a non-detection target nucleotide in a non-target nucleic acid comprising the non-detection target nucleotide, and a hybridization method of using the buffer composition for hybridization.

BACKGROUND ART

In order to more accurately detect a nucleic acid molecule as a measurement target by hybridization with a nucleic acid probe, it is important that the nucleic acid probe accurately recognizes the nucleic acid molecule. Thus, upon performing such hybridization, a method of appropriately adjusting the salt concentration of a reaction solution or the reaction temperature, or a method of using a blocking agent that suppresses non-specific hybridization of a nucleic acid probe with a nucleic acid molecule other than the measurement target, has been conventionally used. Examples of known blocking agents include: nucleic acid components that do not have a nucleotide sequence complementary to a nucleic acid molecule as a measurement target, or to a nucleic acid probe, such as salmon sperm DNA or yeast tRNA; surfactants such as SDS (sodium dodecyl sulfate) and N-lauroyl-sarcosinate (N-LS); and proteins such as bovine serum albumin (BSA) and casein.

However, when there are many nucleic acid molecules that are not measurement targets, the blocking effects of a blocking agent consisting of a nucleic acid component is insufficient. On the other hand, surfactants or proteins used as blocking agents have been problematic in that, since they cannot accurately recognize a nucleotide sequence, their blocking effects are weak.

Patent Literature 1 discloses a method of using a blocker probe that is specifically hybridized with a capture sequence probe comprising a nucleic acid sequence that is hybridized with a specific sequence in a nucleic acid molecule as a measurement target and is also captured on a solid phase. According to the method described in Patent Literature 1, after the capture sequence probe has been hybridized with the nucleic acid molecule as a measurement target, the blocker probe is added to the reaction solution, so that hybridization of an unhybridized capture sequence probe with a cross-reacting nucleic acid sequence existing in the nucleic acid molecule as a measurement target can be prevented, and detection specificity can be thereby improved.

Moreover, Patent Literature 2 discloses the use of an oligonucleotide comprising a modified nucleotide such as a locked nucleic acid (LNA) as a blocking agent, upon detection of a nucleic acid molecule as a measurement target using a microarray.

Further, Patent Literature 3 discloses a method of detecting a nucleic acid molecule as a measurement target with a nucleic acid probe, using a 5'-terminal side blocking nucleic acid that is hybridized with the 5'-terminal side of a detection target nucleotide in a nucleic acid molecule as a measurement target, and a 3'-terminal side blocking nucleic acid that is hybridized with the 3'-terminal side of the detection target nucleotide. According to Patent Literature 3, this method provides high nucleotide sequence specificity in the hybridization of a probe nucleic acid with a target nucleic acid, and thus, this method can improve efficiency and specificity in SNP typing, in which a difference of only one nucleotide in nucleotide sequences needs to be detect with high accuracy, or in detection or separation of nucleic acids having specific nucleotide sequences.

Furthermore. Patent Literature 4 discloses that, when a sample comprises a target nucleic acid comprising a detection target nucleotide and a non-target nucleic acid comprising a non-detection target nucleotide corresponding to the detection target nucleotide, a blocking nucleic acid comprising a nucleotide sequence complementary to the non-target nucleic acid is used, so that the efficiency of detecting the target nucleic acid based on the specific hybridization of the target nucleic acid with a probe nucleic acid can be significantly improved. In particular, in Patent Literature 4, it is described that a blocking nucleic acid preferably has a length that is 60% or more of the nucleotide length of a nucleic acid probe.

CITATION LIST

Patent Literature

Patent Literature 1: JP Patent Publication (Kohyo) No. 2004-511220 A
Patent Literature 2: JP Patent Publication (Kohyo) No. 2005-502346 A
Patent Literature 3: JP Patent Publication (Kokai) No. 2010-200701 A
Patent Literature 4: International Publication WO 2015/045741

SUMMARY OF INVENTION

Technical Problem

As described above, it is an object of the present invention to achieve further excellent efficiency of detecting a target nucleic acid in the case of using a blocking nucleic acid to prevent non-specific hybridization of a non-target nucleic acid with a nucleic acid probe.

Solution to Problem

As a result of intensive studies directed towards achieving the aforementioned object, the present inventors have successfully found the concentration of a blocking nucleic acid, which is capable of effectively suppressing non-specific hybridization of a nucleic acid probe with a non-target nucleic acid, thereby completing the present invention. The present invention includes the following.

(1) A buffer composition used in hybridization of a target nucleic acid comprising a detection target nucleotide with a nucleic acid probe comprising a nucleotide sequence complementary to a region comprising at least the detection target nucleotide in the target nucleic acid, wherein the buffer composition for hybridization contains a blocking nucleic acid comprising a nucleotide sequence complementary to a region comprising at least a non-detection target nucleotide in a non-target nucleic acid, in a concentration of one or more times higher than the concentration of a nucleic acid in a nucleic acid mixture consisting of the target nucleic acid and the non-target nucleic acid comprising the non-detection target nucleotide corresponding to the detection target nucleotide.

(2) The buffer composition for hybridization according to the above (1), wherein the concentration of the blocking nucleic acid is 1 to 5 times higher than the concentration of a nucleic acid in the nucleic acid mixture.

(3) A method of hybridizing a target nucleic acid comprising a detection target nucleotide with a nucleic acid probe comprising a nucleotide sequence complementary to a region comprising at least the detection target nucleotide in the target nucleic acid, wherein the method comprises: mixing a solution comprising a nucleic acid mixture consisting of the target nucleic acid and a non-target nucleic acid comprising a non-detection target nucleotide corresponding to the detection target nucleotide, with a buffer composition for hybridization containing a blocking nucleic acid comprising a nucleotide sequence complementary to a region comprising at least the non-detection target nucleotide in the non-target nucleic acid, in a concentration of one or more times higher than the concentration of the nucleic acid in the nucleic acid mixture; and then hybridizing the nucleic acid probe with the target nucleic acid.

(4) The hybridization method according to the above (3), wherein the buffer composition for hybridization comprises the blocking nucleic acid in a concentration 1 to 5 times higher than the concentration of a nucleic acid in the nucleic acid mixture.

(5) The hybridization method according to the above (3), wherein the solution comprising the nucleic acid mixture contains the target nucleic acid in a concentration of 0.66 nM or more.

(6) The hybridization method according to the above (3), wherein the solution comprising the nucleic acid mixture contains the target nucleic acid at a percentage of 0.5% to 10%, when the total percentage of the target nucleic acid and the non-target nucleic acid is set at 100%.

(7) The hybridization method according to the above (3), wherein the solution comprising the nucleic acid mixture contains the target nucleic acid at a percentage of 0.5% to 10%, when the total percentage of the target nucleic acid and the non-target nucleic acid is set at 100%, and contains the target nucleic acid in a concentration of 0.66 nM or more.

(8) The hybridization method according to the above (3), wherein a mixed solution prepared by mixing the buffer composition for hybridization with the solution comprising the nucleic acid mixture is allowed to come into contact with a microarray formed by immobilizing the nucleic acid probes on a substrate.

(9) The hybridization method according to the above (3), wherein the solution comprising the nucleic acid mixture is a reaction solution obtained after completion of a nucleic acid amplification reaction for amplifying the target nucleic acid, and the reaction solution is mixed with the buffer composition for hybridization.

The present description includes part or all of the contents as disclosed in the description and/or drawings of Japanese Patent Application No. 2016-153058, which is a priority document of the present application.

Advantageous Effects of Invention

According to the buffer composition for hybridization and the hybridization method of the present invention, non-specific hybridization of nucleic acid molecules other than a target nucleic acid comprising a detection target nucleotide with probe nucleic acids can be suppressed. Therefore, by applying the buffer composition for hybridization and the hybridization method according to the present invention, the efficiency of detecting a target nucleic acid, which is based on specific hybridization of the target nucleic acid with a probe nucleic acid, can be significantly improved.

BRIEF DESCRIPTION OF DRAWINGS

FIG. 1-1 is a characteristic diagram showing a difference in the fluorescence intensity ratio, which is obtained by subtracting the fluorescence intensity ratio in the case of hybridization of only wild-type oligo DNA with a DNA chip from the fluorescence intensity ratio of a mutant probe when a nucleic acid mixture of mutant oligo DNA and wild-type oligo DNA is hybridized with a DNA chip in Example 1.

FIG. 1-2 is a characteristic diagram showing a difference in the fluorescence intensity ratio, which is obtained by subtracting the fluorescence intensity ratio in the case of hybridization of only wild-type oligo DNA with a DNA chip from the fluorescence intensity ratio of a mutant probe when a nucleic acid mixture of mutant oligo DNA and wild-type oligo DNA is hybridized with a DNA chip in Example 1.

FIG. 2-1 is a characteristic diagram showing a difference in the fluorescence intensity ratio, which is obtained by subtracting the fluorescence intensity ratio in the case of hybridization of only wild-type oligo DNA with a DNA chip from the fluorescence intensity ratio of a mutant probe when a nucleic acid mixture of mutant oligo DNA and wild-type oligo DNA is hybridized with a DNA chip in Example 2.

FIG. 2-2 is a characteristic diagram showing a difference in the fluorescence intensity ratio, which is obtained by subtracting the fluorescence intensity ratio in the case of hybridization of only wild-type oligo DNA with a DNA chip from the fluorescence intensity ratio of a mutant probe when a nucleic acid mixture of mutant oligo DNA and wild-type oligo DNA is hybridized with a DNA chip in Example 2.

FIG. 3-1 is a characteristic diagram showing a difference in the fluorescence intensity ratio, which is obtained by subtracting the fluorescence intensity ratio in the case of hybridization of only wild-type oligo DNA with a DNA chip from the fluorescence intensity ratio of a mutant probe when a nucleic acid mixture of mutant oligo DNA and wild-type oligo DNA is hybridized with a DNA chip in Example 3.

FIG. 3-2 is a characteristic diagram showing a difference in the fluorescence intensity ratio, which is obtained by subtracting the fluorescence intensity ratio in the case of hybridization of only wild-type oligo DNA with a DNA chip from the fluorescence intensity ratio of a mutant probe when a nucleic acid mixture of mutant oligo DNA and wild-type oligo DNA is hybridized with a DNA chip in Example 3.

FIG. 3-3 is a characteristic diagram showing a difference in the fluorescence intensity ratio, which is obtained by subtracting the fluorescence intensity ratio in the case of hybridization of only wild-type oligo DNA with a DNA chip from the fluorescence intensity ratio of a mutant probe when a nucleic acid mixture of mutant oligo DNA and wild-type oligo DNA is hybridized with a DNA chip in Example 3.

DESCRIPTION OF EMBODIMENTS

The buffer composition for hybridization according to the present invention is a buffer composition used in hybridization of a target nucleic acid comprising a detection target nucleotide with a nucleic acid probe comprising a nucleotide sequence complementary to a region comprising at least the detection target nucleotide in the target nucleic acid. In particular, the buffer composition for hybridization according to the present invention contains a blocking nucleic acid having the function of suppressing non-specific hybridization with nucleic acid probes.

Herein, the term "target nucleic acid" means a nucleic acid molecule containing a detection target nucleotide, namely, a nucleic acid fragment. The target nucleic acid may be either a nucleic acid molecule consisting of DNA, or a nucleic acid molecule consisting of RNA, or it may also be a nucleic acid molecule comprising DNA and RNA (a DNA-RNA complex). In addition, the term "nucleic acid" is used to include adenine, guanine, thymine and uracil, and further, artificial nucleic acids such as peptide nucleic acid (PNA) and locked nucleic acid (LNA).

The term "detection target nucleotide" means, for example, one or more nucleic acid residues at a predetermined position of chromosome, and thus, the type of the detection target nucleotide is not particularly limited. The detection target nucleotide means the type of a specific nucleotide in a nucleotide sequence, such as single nucleotide polymorphism (SNP). For example, when a predetermined single nucleotide polymorphism may have A (adenine) or C (cytosine), either one nucleotide, namely, A (adenine) in the single nucleotide polymorphism may be determined to be a detection target nucleotide. Herein, the detection target nucleotide may be either a major allele or a minor allele in genetic polymorphism, or further, may be or may not be a risk allele.

The target nucleic acid comprising a detection target nucleotide can be prepared by amplifying a predetermined region comprising the detection target nucleotide according to a nucleic acid amplification method. In addition, the target nucleic acid may also be cDNA that is obtained from a transcript collected from an individual organism, tissues or cells according to a reverse transcription reaction. The nucleotide length of the target nucleic acid is not particularly limited. It may be, for example, 60 to 1000 nucleotides, and it is preferably 60 to 500 nucleotides, and more preferably 60 to 200 nucleotides.

Besides, with respect to the target nucleic acid comprising a detection target nucleotide, a nucleic acid molecule (nucleic acid fragment) comprising a non-detection target nucleotide corresponding to the detection target nucleotide is referred to as a "non-target nucleic acid." For instance, among multiple nucleotides that may be disposed at predetermined positions in the chromosome, when one nucleotide is determined to be a detection target nucleotide, nucleotides other than the detection target nucleotide are determined to be non-detection target nucleotides. More specifically, when a single nucleotide polymorphism at a predetermined position may have A (adenine) or C (cytosine), if A (adenine) in the single nucleotide polymorphism is determined to be a detection target nucleotide, C (cytosine) in the single nucleotide polymorphism can be a non-detection target nucleotide.

When a non-detection target nucleotide is present on the chromosome, a non-target nucleic acid comprising the non-detection target nucleotide is obtained simultaneously when the target nucleic acid comprising a detection target nucleotide is obtained, as described above. For example, when the target nucleic acid is obtained by a nucleic acid amplification reaction such as a polymerase chain reaction, if one allele is a non-detection target nucleotide, a non-target nucleic acid is amplified together with the target nucleic acid.

In the present description, a mixture consisting of a target nucleic acid and a non-target nucleic acid is referred to as a "nucleic acid mixture." For example, when the target nucleic acid comprising a detection target nucleotide is obtained by a nucleic acid amplification reaction such as a polymerase chain reaction as described above, the amplified target nucleic acid and non-target nucleic acid are collectively referred to as a "nucleic acid mixture."

In order to detect the target nucleic acid comprising a detection target nucleotide, a nucleic acid probe having a nucleotide sequence complementary to a region comprising at least the detection target nucleotide in the target nucleic acid is used. The type of the nucleic acid probe is not particularly limited, but the nucleic acid probe may have a length of, for example, 10 to 30 nucleotides, and preferably, 15 to 25 nucleotides. In addition, with regard to such a nucleotide complementary to the detection target nucleotide, when nucleotides constituting a nucleic acid probe are seen as a character string, it is preferably positioned in the center of the character string. The phrase "the center of a character string" is used to include a case where the center is shifted by one nucleotide to the 5'-terminal or 3'-terminal direction in the case of a nucleic acid probe consisting of an even number of nucleotides.

In the buffer composition for hybridization according to the present invention, the blocking nucleic acid has a nucleotide sequence complementary to a region comprising a non-detection target nucleotide in a non-target nucleic acid. Hence, the blocking nucleic acid can be hybridized with the non-target nucleic acid under conditions in which the target nucleic acid can be hybridized with the nucleic acid probe.

In particular, in the buffer composition for hybridization according to the present invention, the concentration of the blocking nucleic acid is one or more times higher than the concentration of the nucleic acid in the aforementioned nucleic acid mixture. For example, when the target nucleic acid comprising a detection target nucleotide is obtained by a nucleic acid amplification reaction such as a polymerase chain reaction, the amount of the blocking nucleic acid is adjusted, such that the concentration of the blocking nucleic acid can be one or more times higher than the concentration of a nucleic acid mixture consisting of the amplified target nucleic acid and non-target nucleic acid.

By setting the concentration of the blocking nucleic acid within the above-described range, non-specific hybridization of a non-target nucleic acid with a nucleic acid probe can be more effectively suppressed, and specific hybridization of a target nucleic acid with a nucleic acid probe can be detected with high sensitivity.

On the other hand, in the buffer composition for hybridization according to the present invention, the upper limit of the concentration range of the blocking nucleic acid is not particularly limited, but it is set to be, for example, 5 times or less, with respect to the concentration of the nucleic acid mixture. That is to say, in the buffer composition for hybridization according to the present invention, the concentration range of the blocking nucleic acid is preferably set within the range of 1 to 5 times higher than the concentration of a nucleic acid in the nucleic acid mixture.

Also, the concentration of the nucleic acid in the nucleic acid mixture can be measured according to an ordinary method. For example, the reaction solution obtained after completion of a nucleic acid amplification reaction is purified, the absorbance at a wavelength of 260 nm is then measured using a spectrophotometer, and the measurement value is then converted to the concentration of a nucleic acid. Thereby, the concentration of the nucleic acid in the nucleic acid mixture obtained by the nucleic acid amplification reaction can be measured. Alternatively, the concentration of the nucleic acid in the nucleic acid mixture can also be measured by intercalating an amplification product with fluorescent dye such as SYBR Gold or Pico Green, and then measuring the absorbance around 600 nm. Otherwise, the concentration of the nucleic acid in the nucleic acid mixture can also be measured by detecting an electrophoretic band of the amplification product by performing electrophoresis, and then comparing it with an electrophoretic band of a nucleic acid having a known concentration.

Moreover, the blocking nucleic acid is not particularly limited, but it is preferably designed, such that a difference ($\Delta$Tm) between the Tm value obtained when a target nucleic acid is hybridized with a blocking nucleic acid and the Tm value obtained when a non-target nucleic acid is hybridized with a blocking nucleic acid can be 3° C. or higher, and preferably 5.5° C. or higher. The Tm value regarding the nucleic acid fragment can be calculated, for example, by a calculation method using a nearest neighbor model. As described above, by designing the nucleotide sequence of the blocking nucleic acid, the blocking nucleic acid can be preferentially hybridized with a non-target nucleic acid, so that non-specific hybridization of the non-target nucleic acid with a nucleic acid probe can be more effectively suppressed, and specific hybridization of a target nucleic acid with a nucleic acid probe can be detected with high sensitivity.

Furthermore, although the length of the blocking nucleic acid is not particularly limited, it is preferably a length that is 60% or more of the nucleotide length of the nucleic acid probe, as described in International Publication WO 2015/045741. Further, the blocking nucleic acid is preferably shorter than the nucleotide length of the nucleic acid probe. For example, when the length of the nucleic acid probe consists of 25 nucleotides, the nucleotide length of the blocking nucleic acid preferably consists of 15 to 24 nucleotides.

Further, when nucleotides constituting a blocking nucleic acid are seen as a character string, a nucleotide complementary to a non-detection target nucleotide in the blocking nucleic acid is preferably positioned in the center of the character string. The phrase "the center of a character string" is used to include a case where the center is shifted by one nucleotide to the 5'-terminal or 3'-terminal direction in the case of a blocking nucleic acid consisting of an even number of nucleotides.

Still further, the blocking nucleic acid may comprise a mismatched nucleotide (non-complementary nucleotide) in a position corresponding to a nucleotide other than the non-detection target nucleotide contained in the non-target nucleic acid. When the blocking nucleic acid has a length of 15 nucleotides, the number of mismatched nucleotides may be 1 to 3, and is preferably 1 or 2. In addition, the blocking nucleic acid has a length of 24 nucleotides, the number of mismatched nucleotides may be 1 to 3, and is preferably 1 or 2.

As described above, since the buffer composition for hybridization according to the present invention comprises a blocking nucleic acid in a predetermined concentration range, it can suppress non-specific hybridization of a non-target nucleic acid with a nucleic acid probe, and also, can prevent inhibition of specific hybridization of a target nucleic acid with a nucleic acid probe. For this reason, by using the buffer composition for hybridization according to the present invention, a target nucleic acid can be detected with high accuracy, using the nucleic acid probe, even in a case where, for example, the target nucleic acid is in a low concentration. In addition, by using the buffer composition for hybridization according to the present invention, a target nucleic acid can be detected with high accuracy, using the nucleic acid probe, even in a case where, for example, a non-target nucleic acid that is different from the target nucleic acid in terms of only one nucleotide is present.

In particular, the buffer composition for hybridization according to the present invention is preferably utilized for a nucleic acid mixture comprising a target nucleic acid in a concentration of 0.66 nM or more. When the concentration of the target nucleic acid is within the above-described range, non-specific hybridization of a non-target nucleic acid with a nucleic acid probe can be more effectively suppressed, and specific hybridization of the target nucleic acid with a nucleic acid probe can be detected with high sensitivity.

Moreover, the buffer composition for hybridization according to the present invention is preferably utilized for a nucleic acid mixture comprising a target nucleic acid at a percentage of 50% (non-target nucleic acid: 50%); is more preferably utilized for a nucleic acid mixture comprising a target nucleic acid at a percentage of 10% (non-target nucleic acid: 90%); and is further preferably utilized for a nucleic acid mixture comprising a target nucleic acid at a percentage of 0.5% (non-target nucleic acid: 99.5%). When the percentage of the target nucleic acid in the nucleic acid mixture is within the above-described range, non-specific hybridization of a non-target nucleic acid with a nucleic acid probe can be more effectively suppressed, and specific hybridization of the target nucleic acid with a nucleic acid probe can be detected with high sensitivity.

Furthermore, the buffer composition for hybridization according to the present invention is preferably utilized for a nucleic acid mixture comprising a target nucleic acid in a concentration of 3.3 nM or more, and more preferably 0.66 nM or more, and also comprising the target nucleic acid at a percentage of 10% or less (non-target nucleic acid: 90% or more), and more preferably, the target nucleic acid at a percentage of 0.5% or more (non-target nucleic acid: less than 99.5% or more). When the concentration and percentage of the target nucleic acid in the nucleic acid mixture is within the above-described range, non-specific hybridization of a non-target nucleic acid with a nucleic acid probe can be more effectively suppressed, and specific hybridization of the target nucleic acid with a nucleic acid probe can be detected with high sensitivity.

Herein, the upper limit of the percentage of the target nucleic acid contained in the nucleic acid mixture is not particularly limited, but it is preferably 50% or less, and more preferably 10% or less, for example, when the total percentage of the target nucleic acid and the non-target nucleic acid is set at 100%. When the percentage of the target nucleic acid in the nucleic acid mixture exceeds the above-described range, it may cause inconvenience such that the target nucleic acid cannot be detected even if a blocking nucleic acid is added, or the target nucleic acid can be detected even if a blocking nucleic acid is not added.

The buffer composition for hybridization according to the present invention can be used in all systems, as long as the systems include hybridization that means a complementary bond between nucleic acid molecules. That is, the buffer composition for hybridization according to the present invention can be used in Southern hybridization, Northern hybridization, and in situ hybridization. In particular, the buffer composition for hybridization according to the present invention is preferably used in a system, in which nucleic acid probes are immobilized on a carrier (including a substrate, a hollow fiber, and a fine particle) and the immobilized nucleic acid probes are used to detect (including qualify and quantify) a target nucleic acid. More specifically, the buffer composition for hybridization according to the present invention is most preferably used, when a target nucleic acid is detected using a DNA microarray (DNA chip), in which nucleic acid probes are immobilized on a substrate.

Hereafter, a system, in which the buffer composition for hybridization according to the present invention is used to detect a target nucleic acid, using a DNA microarray (DNA chip), will be exemplarily described. It is to be noted that the embodiment of the buffer composition for hybridization according to the present invention is not limited to the following examples.

There are the following examples: an example, in which the 12th codon (Codon 12) in K-ras (v-Ki-ras2 Kirsten rat sarcoma viral oncogene homolog) is used to be a target nucleic acid as a measurement target comprising a wild-type GGTGGC sequence; and an example, in which the 117th codon (Codon 117) is used to be a target nucleic acid as a measurement target comprising a wild-type AAA sequence. Thus, a nucleic acid comprising a sequence, in which Codon 12 and/or Codon 117 are mutants, is a non-target nucleic acid. Regarding Codon 12, mutations such as p.G12S (c.34G>A), p.G12C (c.34G>T), p.G12R (c.34G>C), p.G12D (c.35G>A), p.G12V (c.35G>T) and p.G12A (c.35G>C) have been known. On the other hand, regarding Codon 117, mutations such as p.K117N (c.351A>C) and p.K117N (c.351A>T) have been known.

When a plurality of non-target nucleic acids are present, blocking nucleic acids may be prepared for all of the non-target nucleic acids, or may also be prepared for some non-target nucleic acids.

The nucleic acid probe and the blocking nucleic acid are more preferably single-stranded DNAs. The nucleic acid probe and the blocking nucleic acid can be obtained, for example, by chemical synthesis using a nucleic acid synthesizer. Examples of the nucleic acid synthesizer that can be used herein include apparatuses called a DNA synthesizer, a full automatic nucleic acid synthesizer, an automated polynucleotide synthesizer, etc.

In the present example, the 5'-terminus of a nucleic acid probe is modified with a linker, and the probe is then immobilized on a carrier, so that it is preferably used in the form of a microarray. The linker may be or may not be constituted with specific nucleotides of a single type. The linker is preferably constituted with a nucleotide sequence that is not associated with hybridization of a target nucleic acid with a nucleic acid probe.

As materials for the carrier, materials known in the present technical field can be used, and are not particularly limited. Examples of the material include: noble metals such as platinum, platinum black, gold, palladium, rhodium, silver, mercury, tungsten and the compounds thereof, and conductive materials such as graphite and carbon fiber; silicon materials, including as typical examples, single crystal silicon, amorphous silicon, silicon carbide, silicon oxide and silicon nitride, and complex materials of these silicon materials, including, as a typical example, SOI (silicon on insulator); inorganic materials such as glass, quartz glass, alumina, sapphire, ceramics, forsterite, and photosensitive glass; and organic materials such as polyethylene, ethylene, polypropylene, cyclic polyolefin, polyisobutylene, polyethylene terephthalate, unsaturated polyester, a fluorine-containing resin, polyvinyl chloride, polyvinylidene chloride, polyvinyl acetate, polyvinyl alcohol, polyvinyl acetal, an acrylic resin, polyacrylonitrile, polystyrene, an acetal resin, polycarbonate, polyamide, a phenolic resin, a urea resin, an epoxy resin, a melamine resin, a styrene-acrylonitrile copolymer, an acrylonitrile-butadienestyrene copolymer, polyphenylene oxide and polysulfone. The shape of the carrier is not particularly limited, either, but it is preferably platy.

As such a carrier, a carrier, which has a carbon layer such as diamond liker carbon (DLC) and a chemically modifying group such as an amino group, a carboxyl group, an epoxy group, a formyl group, a hydroxyl group and an active ester group on the surface thereof, is preferably used. Examples of the carrier having a carbon layer and a chemically modifying group on the surface thereof include: a carrier having a carbon layer and a chemically modifying group on the surface of a substrate; and a carrier having a chemically modifying group on the surface of a substrate consisting of a carbon layer. As materials for the substrate, materials known in the present technical field can be used, and are not particularly limited. The same materials as those for the carrier, which are mentioned above, can be used.

Using the thus produced DNA microarray, a target nucleic acid can be detected in a subject. The detection method comprises a step of extracting DNA from a subject-derived sample, a step of amplifying a region comprising Codon 12 and/or Codon 117 in K-ras, using the extracted DNA as a template, and a step of detecting the amplified nucleic acid using the DNA microarray.

The subject is generally a human, and examples of the subject include patients affected with colorectal cancer including colon cancer and rectal cancer, head and neck cancer, or non-small cell lung cancer. Otherwise a healthy person who is not affected with the aforementioned cancers may also be used as a subject. Furthermore, a patient who is affected with EGFR-positive progressive and/or recurrent colon and/or rectal cancer may also be used as a subject. The subject-derived sample is not particularly limited. Examples of the subject-derived sample include a blood-related sample (blood, serum, plasma, etc.), lymph fluid, feces, and disintegrated products and extracts of cancer cells, tissues or organs.

First, DNA is extracted from a sample collected from a subject. The extraction means are not particularly limited. For example, a DNA extraction method using phenol/chloroform, ethanol, sodium hydroxide, CTAB. etc. can be used.

Then, an amplification reaction is carried out using the obtained DNA as a template, and a nucleic acid encoding a K-RAS gene, and preferably, DNA is amplified. As such an amplification reaction, a polymerase chain reaction (PCR), LAMP (Loop-Mediated Isothermal Amplification), ICAN (Isothermal and Chimeric primer-initiated Amplification of Nucleic acids) method, and the like can be applied. In the amplification reaction, in order to identify the amplified region, a label is desirably added. At this time, a method of labeling the amplified nucleic acid is not particularly limited. For example, a method of previously labeling primers used in the amplification reaction may be applied, or a method of using a labeled nucleotide as a substrate in the amplification reaction may also be applied. The labeling substance is not particularly limited. Examples of the labeling substance that can be used herein include radioactive isotopes, fluorescent dyes, and organic compounds such as digoxigenin (DIG) and biotin.

Moreover, this reaction system is a reaction system comprising a buffer, heat-resistant DNA polymerase, primers specific to the K-RAS gene, labeled nucleotide triphosphate (specifically, nucleotide triphosphate to which a fluorescent labelling compound or the like has been added), nucleotide triphosphate, magnesium chloride, etc., which are necessary for nucleic acid amplification and/or labeling.

Primers used in the amplification reaction are not particularly limited, as long as they can specifically amplify a region comprising Codon 12 and/or Codon 117 in K-ras. A person skilled in the art could appropriately design such primers. For example, a primer set consisting of:

```
                                    (SEQ ID NO: 17)
Primer 1:    5'-gtgtgacatgttctaatatagtcac-3'
and (SEQ ID NO: 18)
Primer 2:    5'-gaatggtcctgcaccagtaa-3'
``` is used for Codon 12. In addition, a primer set consisting of:

```
                                    (SEQ ID NO: 19)
Primer 3:    5'-ctctgaagatgtacctatggtc-3'
and (SEQ ID NO: 20)
Primer 4:    5'-gtctactgttctagaaggcaaat-3',
``` is used for Codon 117.

The above-obtained, amplified nucleic acid comprises a target nucleic acid and a non-target nucleic acid. A hybridization reaction of a nucleic acid probe with the target nucleic acid is carried out, and the amount of nucleic acid hybridized with the nucleic acid probe can be measured, for example, by detecting a labeled substance. With regard to signals from such a labeled substance, in the case of using fluorescent labeling, the signal intensity can be quantified by detecting fluorescent signals using a fluorescent scanner, and then analyzing the detected signals using image analysis software. Moreover, the amplified nucleic acid hybridized with the nucleic acid probe can also be quantified, for example, by preparing a calibration curve using a sample comprising a known amount of DNA.

At this time, by using the aforementioned buffer composition for hybridization according to the present invention, non-specific hybridization of a non-target nucleic acid with a nucleic acid probe can be suppressed. The hybridization reaction using the buffer composition for hybridization is preferably carried out under stringent conditions. The term "stringent conditions" is used to mean conditions under which a specific hybrid is formed and a non-specific hybrid is not formed. Such stringent conditions mean, for example, conditions under which a hybridization reaction is carried out at 50° C. for 16 hours and the reaction product is then washed with 2×SSC/0.2% SDS at 25° C. for 10 minutes, and then with 2×SSC at 25° C. for 5 minutes. That is to say, the buffer composition for hybridization according to the present invention may comprise salts necessary for the hybridization reaction, for example, SSC, and a known blocking agent such as SDS.

Alternatively, the reaction solution comprising a target nucleic acid and a non-target nucleic acid after completion of the amplification reaction has been previously mixed with the buffer composition for hybridization according to the present invention, so that specific hybridization of the non-target nucleic acid with a blocking nucleic acid has been carried out, and thereafter, the reaction solution may be allowed to come into contact with a DNA microarray, so that the hybridization reaction of the target nucleic acid with a nucleic acid probe may be progressed. Otherwise, the reaction solution comprising a target nucleic acid and a non-target nucleic acid after completion of the amplification reaction may be mixed with the buffer composition for hybridization according to the present invention on a DNA microarray, so that specific hybridization of the non-target nucleic acid with a blocking nucleic acid and specific hybridization of the target nucleic acid with a nucleic acid probe may be simultaneously progressed.

EXAMPLES

Hereinafter, the present invention will be described in more detail in the following examples. However, these examples are not intended to limit the technical scope of the present invention.

Example 1

In the present example, the wild-type nucleotide sequence (AAA) of Codon 117 in K-ras was determined to be non-detection target nucleotides, and mutant nucleotide sequences (AAC and AAT) were determined to be detection target nucleotides. As a wild-type specimen, oligo DNA consisting of 36 nucleotides having the wild-type nucleotide sequence (AAA) of Codon 117 in the center thereof (wild-type oligo DNA 1) was used. As mutant specimens, oligo DNAs each consisting of 36 nucleotides having the mutant nucleotide sequence (AAC or AAT) of Codon 117 in the center thereof (mutant oligo DNAs 1 and 2) were used. The wild-type oligo DNA 1 and the mutant oligo DNAs 1 and 2 each had a 5'-terminus labeled with Cyanine5 (Cy5). The concentration of the mutant oligo DNA was set at 3.3 nM, and the wild-type oligo DNA was mixed with the mutant oligo DNAs to result in a mutation percentage of 0.5%, 10% or 50%, thereby preparing a nucleic acid mixture.

In the present example, a blocking nucleic acid 1 complementary to non-detection target nucleotides, namely, the wild-type nucleotide sequence (AAA), was designed (sequence: GCAAATCACAtttATTCCTA; SEQ ID NO: 4). A buffer composition for hybridization comprising the blocking nucleic acid was mixed with the above-obtained nucleic acid mixture to prepare a hybridization reaction solution (containing 1×SSC/0.1% SDS).

The hybridization reaction solution was added dropwise onto a DNA chip, and a hybridization cover was applied thereon, followed by performing a reaction at 45° C. for 1 hour in a hybridization chamber. As such a DNA chip. GENE SILICON® (manufactured by Toyo Kohan Co., Ltd.) was used. Besides, this DNA chip comprises a nucleic acid probe 1 (GCAAATCACAtttATTTCCTA (SEQ ID NO: 5)) for detecting the wild-type oligo DNA, a nucleic acid probe 2 (CAAATCACAgttATTCCT (SEQ ID NO: 6)) for detecting the mutant oligo DNA 1, and a nucleic acid probe 3 (GCAAATCACAattATTTCCTA (SEQ ID NO: 7)) for detecting the mutant oligo DNA 2.

The nucleotide sequences of the wild-type oligo DNA 1, the mutant oligo DNAs 1 and 2, the blocking nucleic acid 1, and the nucleic acid probes 1 to 3 are collectively shown in Table 1.

TABLE 1

| Name | SEQ ID NO: | Sequence (5' to 3') | Number of nucleotides |
|---|---|---|---|
| Wild-type oligo DNA 1 | 1 | Cy5-TATGGTCCTAGTAGGAAATAAATGTGATTTGCCTTC | 36 |
| Mutant oligo DNA 1 | 2 | Cy5-TATGGTCCTAGTAGGAAATAACTGTGATTTGCCTTC | 36 |
| Mutant oligo DNA 2 | 3 | Cy5-TATGGTCCTAGTAGGAAATAATTGTGATTTGCCTTC | 36 |
| Blocking nucleic acid 1 | 4 | GCAAATCACATTTATTTCCTA | 21 |
| Nucleic acid probe 1 | 5 | GCAAATCACATTTATTTCCTA | 21 |
| Nucleic acid probe 2 | 6 | CAAATCACAGTTATTTCCT | 19 |
| Nucleic acid probe 3 | 7 | GCAAATCACAATTATTTCCTA | 21 |

The composition ratio between mutant oligo DNA and wild-type oligo DNA comprised in a nucleic acid mixture, the concentration of a blocking nucleic acid, the equivalent amount of a blocking nucleic acid, and the like, in each experimental plot, are collectively shown in Table 2-1 to Table 2-3.

TABLE 2-1

| Test conditions | Mutant oligo DNA SEQ ID NO: | Mutant oligo DNA Concentration | Wild-type oligo DNA SEQ ID NO: | Wild-type oligo DNA Concentration | Mutation percentage | Blocking nucleic acid SEQ ID NO: | Blocking nucleic acid Concentration | Amount of blocking nucleic acid to nucleic acid mixture | Fluorescence intensity ratio Nucleic acid probe 2 | Fluorescence intensity ratio Nucleic acid probe 3 |
|---|---|---|---|---|---|---|---|---|---|---|
| A-1-1 | 2 | 3.3 nM | 1 | 3.3 nM | 50% | 4 | 0 nM | 0 time | 1.092 | — |
| A-1-2 | 2 | 3.3 nM | 1 | 3.3 nM | 50% | 4 | 3.3 nM | 0.5 times | 1.024 | — |
| A-1-3 | 2 | 3.3 nM | 1 | 3.3 nM | 50% | 4 | 6.6 nM | 1 time | 1.013 | — |
| A-1-4 | 2 | 3.3 nM | 1 | 3.3 nM | 50% | 4 | 19.8 nM | 3 times | 5.356 | — |
| A-1-5 | 2 | 3.3 nM | 1 | 3.3 nM | 50% | 4 | 33 nM | 5 times | 5.928 | — |
| A-1-6 | 2 | 3.3 nM | 1 | 3.3 nM | 50% | 4 | 66 nM | 10 times | 0.000 | — |
| A-2-1 | 2 | 3.3 nM | 1 | 29.7 nM | 10% | 4 | 0 nM | 0 time | 0.622 | — |
| A-2-2 | 2 | 3.3 nM | 1 | 29.7 nM | 10% | 4 | 16.5 nM | 0.5 times | 0.629 | — |
| A-2-3 | 2 | 3.3 nM | 1 | 29.7 nM | 10% | 4 | 33 nM | 1 time | 0.802 | — |
| A-2-4 | 2 | 3.3 nM | 1 | 29.7 nM | 10% | 4 | 99 nM | 3 times | 2.420 | — |
| A-2-5 | 2 | 3.3 nM | 1 | 29.7 nM | 10% | 4 | 165 nM | 5 times | 3.720 | — |
| A-2-6 | 2 | 3.3 nM | 1 | 29.7 nM | 10% | 4 | 330 nM | 10 times | 0.000 | — |
| A-3-1 | 2 | 3.3 nM | 1 | 656.7 nM | 0.5% | 4 | 0 nM | 0 time | 0.533 | — |
| A-3-2 | 2 | 3.3 nM | 1 | 656.7 nM | 0.5% | 4 | 330 nM | 0.5 times | 0.560 | — |
| A-3-3 | 2 | 3.3 nM | 1 | 656.7 nM | 0.5% | 4 | 660 nM | 1 time | 0.506 | — |
| A-3-4 | 2 | 3.3 nM | 1 | 656.7 nM | 0.5% | 4 | 1980 nM | 3 times | 0.000 | — |
| A-3-5 | 2 | 3.3 nM | 1 | 656.7 nM | 0.5% | 4 | 3300 nM | 5 times | 0.000 | — |
| A-3-6 | 2 | 3.3 nM | 1 | 656.7 nM | 0.5% | 4 | 6600 nM | 10 times | 0.000 | — |

TABLE 2-2

| Test conditions | Mutant oligo DNA SEQ ID NO: | Mutant oligo DNA Concentration | Wild-type oligo DNA SEQ ID NO: | Wild-type oligo DNA Concentration | Mutation percentage | Blocking nucleic acid SEQ ID NO: | Blocking nucleic acid Concentration | Amount of blocking nucleic acid to nucleic acid mixture | Fluorescence intensity ratio Nucleic acid probe 2 | Fluorescence intensity ratio Nucleic acid probe 3 |
|---|---|---|---|---|---|---|---|---|---|---|
| A-4-1 | 3 | 3.3 nM | 1 | 3.3 nM | 50% | 4 | 0 nM | 0 time | — | 1.320 |
| A-4-2 | 3 | 3.3 nM | 1 | 3.3 nM | 50% | 4 | 3.3 nM | 0.5 times | — | 1.340 |
| A-4-3 | 3 | 3.3 nM | 1 | 3.3 nM | 50% | 4 | 6.6 nM | 1 time | — | 1.774 |
| A-4-4 | 3 | 3.3 nM | 1 | 3.3 nM | 50% | 4 | 19.8 nM | 3 times | — | 4.266 |
| A-4-5 | 3 | 3.3 nM | 1 | 3.3 nM | 50% | 4 | 33 nM | 5 times | — | 5.647 |
| A-4-6 | 3 | 3.3 nM | 1 | 3.3 nM | 50% | 4 | 66 nM | 10 times | — | 0.000 |
| A-5-1 | 3 | 3.3 nM | 1 | 29.7 nM | 10% | 4 | 0 nM | 0 time | — | 0.822 |
| A-5-2 | 3 | 3.3 nM | 1 | 29.7 nM | 10% | 4 | 16.5 nM | 0.5 times | — | 0.940 |
| A-5-3 | 3 | 3.3 nM | 1 | 29.7 nM | 10% | 4 | 33 nM | 1 time | — | 1.005 |
| A-5-4 | 3 | 3.3 nM | 1 | 29.7 nM | 10% | 4 | 99 nM | 3 times | — | 2.610 |
| A-5-5 | 3 | 3.3 nM | 1 | 29.7 nM | 10% | 4 | 165 nM | 5 times | — | 3.494 |
| A-5-6 | 3 | 3.3 nM | 1 | 29.7 nM | 10% | 4 | 330 nM | 10 times | — | 0.000 |
| A-6-1 | 3 | 3.3 nM | 1 | 656.7 nM | 0.5% | 4 | 0 nM | 0 time | — | 0.680 |

TABLE 2-2-continued

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Amount of blocking nucleic acid to nucleic acid mixture | Fluorescence intensity ratio Nucleic acid probe 2 | Nucleic acid probe 3 |
|---|---|---|---|---|---|---|---|---|---|---|
| A-6-2 | 3 | 3.3 nM | 1 | 656.7 nM | 0.5% | 4 | 330 nM | 0.5 times | — | 0.633 |
| A-6-3 | 3 | 3.3 nM | 1 | 656.7 nM | 0.5% | 4 | 660 nM | 1 time | — | 0.698 |
| A-6-4 | 3 | 3.3 nM | 1 | 656.7 nM | 0.5% | 4 | 1980 nM | 3 times | — | 0.659 |
| A-6-5 | 3 | 3.3 nM | 1 | 656.7 nM | 0.5% | 4 | 3300 nM | 5 times | — | 0.000 |
| A-6-6 | 3 | 3.3 nM | 1 | 656.7 nM | 0.5% | 4 | 6600 nM | 10 times | — | 0.000 |

TABLE 2-3

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Amount of blocking nucleic acid to nucleic acid mixture | Fluorescence intensity ratio Nucleic acid probe 2 | Nucleic acid probe 3 |
|---|---|---|---|---|---|---|---|---|---|---|
| B-1-1 | — | 0 nM | 1 | 6.6 nM | 0% | 4 | 0 nM | 0 time | 0.063 | 0.261 |
| B-1-2 | — | 0 nM | 1 | 6.6 nM | 0% | 4 | 3.3 nM | 0.5 times | 0.074 | 0.289 |
| B-1-3 | — | 0 nM | 1 | 6.6 nM | 0% | 4 | 6.6 nM | 1 time | 0.070 | 0.248 |
| B-1-4 | — | 0 nM | 1 | 6.6 nM | 0% | 4 | 19.8 nM | 3 times | 0.000 | 0.000 |
| B-1-5 | — | 0 nM | 1 | 6.6 nM | 0% | 4 | 33 nM | 5 times | 0.000 | 0.000 |
| B-1-6 | — | 0 nM | 1 | 6.6 nM | 0% | 4 | 66 nM | 10 time | 0.000 | 0.000 |
| B-2-1 | — | 0 nM | 2 | 33 nM | 0% | 4 | 0 nM | 0 time | 0.280 | 0.530 |
| B-2-2 | — | 0 nM | 1 | 33 nM | 0% | 4 | 16.5 nM | 0.5 times | 0.248 | 0.598 |
| B-2-3 | — | 0 nM | 1 | 33 nM | 0% | 4 | 33 nM | 1 time | 0.121 | 0.372 |
| B-2-4 | — | 0 nM | 1 | 33 nM | 0% | 4 | 99 nM | 3 times | 0.067 | 0.116 |
| B-2-5 | — | 0 nM | 1 | 33 nM | 0% | 4 | 165 nM | 5 times | 0.000 | 0.000 |
| B-2-6 | — | 0 nM | 1 | 33 nM | 0% | 4 | 330 nM | 10 times | 0.000 | 0.000 |
| B-3-1 | — | 0 nM | 1 | 660 nM | 0% | 4 | 0 nM | 0 time | 0.535 | 0.608 |
| B-3-2 | — | 0 nM | 1 | 660 nM | 0% | 4 | 330 nM | 0.5 times | 0.390 | 0.670 |
| B-3-3 | — | 0 nM | 1 | 660 nM | 0% | 4 | 660 nM | 1 time | 0.266 | 0.432 |
| B-3-4 | — | 0 nM | 1 | 660 nM | 0% | 4 | 1980 nM | 3 times | 0.096 | 0.176 |
| B-3-5 | — | 0 nM | 1 | 660 nM | 0% | 4 | 3300 nM | 5 times | 0.000 | 0.000 |
| B-3-6 | — | 0 nM | 1 | 660 nM | 0% | 4 | 6600 nM | 10 times | 0.000 | 0.000 |

After completion of the reaction, the DNA chip was washed by shaking it with 1×SSC/0.1% SDS 30 times, and then, with 1×SSC 30 times. Thereafter, a cover film was applied on the DNA chip, and fluorescence intensity was then measured using a bioshot. At this time, when the concentration of the nucleic acid mixture was less than 660 nM, the exposure time of a CCD camera was changed to 2 seconds, 5 seconds, 10 seconds, and 20 seconds. On the other hand, when the concentration of the nucleic acid mixture was 660 nM, the exposure time of the CCD camera was changed to 1 second, 3 seconds, 5 seconds, and 7 seconds, thereby obtaining fluorescence intensity.

The fluorescence intensity of the nucleic acid probe 2 (for detection of mutant oligo DNA 1) was divided by the fluorescence intensity of the nucleic acid probe 1 (for detection of wild-type oligo DNA) to calculate a fluorescence intensity ratio. In addition, the fluorescence intensity of the nucleic acid probe 3 (for detection of mutant oligo DNA 2) was divided by the fluorescence intensity of the nucleic acid probe 1 to calculate a fluorescence intensity ratio. When the detected fluorescence intensity was 2000 or less, it was determined to be lack of intensity, and thus, the intensity ratio was determined to 0 (error). When the detected fluorescence intensity was 50000 or more, it was determined to be close to the intensity detection saturation region, and thus, the intensity ratio was determined to 0 (error). Tables 2-1 to 2-3 show the largest fluorescence intensity ratio in each exposure time.

From the fluorescence intensity ratio obtained by hybridizing the nucleic acid mixture of the mutant oligo DNA and the wild-type oligo DNA with each of the nucleic acid probes 1 to 3 (Table 2-1 and Table 2-2), the fluorescence intensity ratio obtained by hybridizing only the wild-type oligo DNA with each of the nucleic acid probes 1 to 3 (Table 2-3) was subtracted, so that a difference in the fluorescence intensity ratio was obtained for each exposure time. Such a difference in the fluorescence intensity ratio was obtained for each exposure time, and the largest values are shown in Table 3-1, Table 3-2, and FIG. 1.

In addition, using the obtained fluorescence intensity and the measurement results shown in FIG. 1, the mutation judgments [1], [2] and [3] were carried out using a DNA chip, as described below, and the obtained judgment results are shown in Table 3-1 and Table 3-2. It is to be noted that the term "AB-1-1" in the column "Test conditions," for example, in FIG. 1, Table 3-1 and Table 3-2 is based on the test results obtained under the test conditions "A-1-1" shown in Table 2-1 and the test results obtained under the test conditions "B-1-1" shown in Table 2-3.

TABLE 3-1

| Test condition | Difference in fluorescence intensity ratio | Judgment result [1] | Judgment result [2] | Judgment result [3] |
|---|---|---|---|---|
| AB-1-1 | 1.032 | ○ | ○ | — |
| AB-1-2 | 0.951 | ○ | ○ | X |
| AB-1-3 | 0.949 | ○ | ○ | X |
| AB-1-4 | 0.000 | X | X | X |
| AB-1-5 | 0.000 | X | X | X |
| AB-1-6 | 0.000 | X | X | X |
| AB-2-1 | 0.342 | X | ○ | — |
| AB-2-2 | 0.382 | X | ○ | X |
| AB-2-3 | 0.685 | X | ○ | ○ |
| AB-2-4 | 2.368 | ○ | ○ | ○ |
| AB-2-5 | 0.000 | X | X | X |
| AB-2-6 | 0.000 | X | X | X |
| AB-3-1 | 0.000 | X | X | — |
| AB-3-2 | 0.170 | X | ○ | ○ |
| AB-3-3 | 0.246 | X | ○ | ○ |
| AB-3-4 | 0.308 | X | ○ | ○ |
| AB-3-5 | 0.000 | X | X | X |
| AB-3-6 | 0.000 | X | X | X |

TABLE 3-2

| Test condition | Difference in fluorescence intensity ratio | Judgment result [1] | Judgment result [2] | Judgment result [3] |
|---|---|---|---|---|
| AB-4-1 | 1.059 | ○ | ○ | — |
| AB-4-2 | 1.095 | ○ | ○ | X |
| AB-4-3 | 1.536 | ○ | ○ | ○ |
| AB-4-4 | 0.000 | X | X | X |
| AB-4-5 | 0.000 | X | X | X |
| AB-4-6 | 0.000 | X | X | X |
| AB-5-1 | 0.292 | X | ○ | — |
| AB-5-2 | 0.313 | X | ○ | X |
| AB-5-3 | 0.633 | ○ | ○ | ○ |
| AB-5-4 | 2.417 | ○ | ○ | ○ |
| AB-5-5 | 0.000 | X | X | X |
| AB-5-6 | 0.000 | X | X | X |
| AB-6-1 | 0.073 | X | X | — |
| AB-6-2 | 0.000 | X | X | X |
| AB-6-3 | 0.266 | X | ○ | ○ |
| AB-6-4 | 0.510 | X | ○ | ○ |
| AB-6-5 | 0.000 | X | X | X |
| AB-6-6 | 0.000 | X | X | X |

First, with regard to the mutation judgment [1], when a nucleic acid mixture of mutant oligo DNA and wild-type oligo DNA was hybridized with the nucleic acid probes 1 to 3, the fluorescence intensity of the nucleic acid probe 2 or 3 was higher than the fluorescence intensity of the nucleic acid probe 1 (fluorescence intensity ratio>1), and when only the wild-type oligo DNA was hybridized with the nucleic acid probes 1 to 3, the fluorescence intensity of the nucleic acid probe 2 or 3 was lower than the fluorescence intensity of the nucleic acid probe 1 (fluorescence intensity ratio<1), the mutation judgment results were defined as "○". That is, it means that, in the positive judgment in the mutation judgment [1], since the fluorescence intensity of the nucleic acid probe 2 or 3 was higher in the presence of mutant oligo DNA and the fluorescence intensity of the nucleic acid probe 1 was higher in the absence of the mutant oligo DNA, these are conditions under which a mutation judgment is easily carried out.

From the results shown in Table 3-1 and Table 3-2, in the mutation judgment [1], it was judged to be positive with 0 to 1 time the blocking nucleic acid at a mutation percentage of 50%, and it was judged to be positive with only 3 times the blocking nucleic acid at a mutation percentage of 10%.

Subsequently, with regard to the mutation judgment [2], from the fluorescence intensity ratio obtained by hybridizing the nucleic acid mixture of the mutant oligo DNA and the wild-type oligo DNA with each of the nucleic acid probes 1 to 3, the fluorescence intensity ratio obtained by hybridizing only the wild-type oligo DNA with each of the nucleic acid probes 1 to 3 was subtracted. With regard to the thus obtained difference in the fluorescence intensity ratio, if a difference in the intensity ratio at each exposure time>0.1, the mutation judgment results were defined as "○". That is, it means that, in the positive judgment in the mutation judgment [2], even if the mutation percentage of mutant oligo DNA contained in the nucleic acid mixture of the mutant oligo DNA and the wild-type oligo DNA is low, and also even if the fluorescence intensity of the nucleic acid probe 2 or 3 is lower than the fluorescence intensity of the nucleic acid probe 1, it is possible to perform a positive judgment using a DNA chip by comparing the obtained fluorescence intensity with the fluorescence intensity in the absence of the mutant oligo DNA.

From the results shown in Table 3-1 and Table 3-2, it was found that, in the mutation judgment [2], it is possible to carry out a positive judgement with 0 to 1 time the blocking nucleic acid at a mutation percentage of 50%, it is possible to carry out a positive judgement with 0 to 3 times the blocking nucleic acid at a mutation percentage of 10%, and it is possible to carry out a positive judgement with 1 to 3 times the blocking nucleic acid at a mutation percentage of 0.5%. Thus, it was found that it is possible to carry out a positive judgment even under conditions of a mutation percentage of 0.5%.

Subsequently, with regard to the mutation judgment [3], from a difference in the fluorescence intensity ratio under conditions of addition of the blocking nucleic acid, a difference in the fluorescence intensity ratio under conditions of non-addition of the blocking nucleic acid was subtracted to calculate a double difference. If this double difference in the intensity ratio>0.1, the mutation judgment results were defined as "○". That is, it means that, in the positive judgment in the mutation judgment [3], the judgment sensitivity was higher under the conditions of addition of the blocking nucleic acid than under conditions of non-addition of the blocking nucleic acid, and thus that addition of the blocking nucleic acid is effective for the mutation judgment.

From the results shown in Table 3-1 and Table 3-2, it is found that it becomes almost impossible to make judgement at a mutation percentage of 50%, and that the effects of the blocking nucleic acid cannot be obtained. On the other hand, since a positive judgment could be performed at 1 to 3 times if the mutation percentage was 10% and 0.5%, the blocking nucleic acid added in an amount of 1 to 3 times into a nucleic acid mixture containing 3.3 nM mutant oligo DNA at a mutation percentage of 0.5% to 10% was found to be an additive amount preferable to the mutation judgment.

Example 2

In the present example, as with Example 1, the wild-type nucleotide sequence (AAA) of Codon 117 in K-ras was determined to be non-detection target nucleotides, and mutant nucleotide sequences (AAC and AAT) were determined to be detection target nucleotides. Then, an experiment was carried out in the same manner as that of Example 1, with the exception that the concentration of a specimen having such a mutant nucleotide sequence was set at 0.66 nM.

The composition ratio between mutant oligo DNA and wild-type oligo DNA comprised in a nucleic acid mixture, the concentration of a blocking nucleic acid, and the equivalent amount of a blocking nucleic acid, in each experimental plot, are collectively shown in Table 4-1 to Table 4-3.

TABLE 4-1

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Equivalent of blocking nucleic acid to nucleic acid mixture | Fluorescence intensity ratio Nucleic acid probe 2 | Nucleic acid probe 3 |
|---|---|---|---|---|---|---|---|---|---|---|
| C-1-1 | 2 | 0.66 nM | 1 | 0.66 nM | 50% | 4 | 0 nM | 0 time | 0.750 | — |
| C-1-2 | 2 | 0.66 nM | 1 | 0.66 nM | 50% | 4 | 0.66 nM | 0.5 times | 0.578 | — |
| C-1-3 | 2 | 0.66 nM | 1 | 0.66 nM | 50% | 4 | 1.32 nM | 1 time | 0.579 | — |
| C-1-4 | 2 | 0.66 nM | 1 | 0.66 nM | 50% | 4 | 3.96 nM | 3 times | 0.586 | — |
| C-1-5 | 2 | 0.66 nM | 1 | 0.66 nM | 50% | 4 | 6.6 nM | 5 times | 0.535 | — |
| C-1-6 | 2 | 0.66 nM | 1 | 0.66 nM | 50% | 4 | 13.2 nM | 10 times | 0.000 | — |
| C-2-1 | 2 | 0.66 nM | 1 | 5.94 nM | 10% | 4 | 0 nM | 0 time | 0.424 | — |
| C-2-2 | 2 | 0.66 nM | 1 | 5.94 nM | 10% | 4 | 3.3 nM | 0.5 times | 0.300 | — |
| C-2-3 | 2 | 0.66 nM | 1 | 5.94 nM | 10% | 4 | 6.6 nM | 1 time | 0.245 | — |
| C-2-4 | 2 | 0.66 nM | 1 | 5.94 nM | 10% | 4 | 19.8 nM | 3 times | 0.000 | — |
| C-2-5 | 2 | 0.66 nM | 1 | 5.94 nM | 10% | 4 | 33 nM | 5 times | 0.000 | — |
| C-2-6 | 2 | 0.66 nM | 1 | 5.94 nM | 10% | 4 | 66 nM | 10 times | 0.000 | — |
| C-3-1 | 2 | 0.66 nM | 1 | 131.34 nM | 0.5% | 4 | 0 nM | 0 time | 0.358 | — |
| C-3-2 | 2 | 0.66 nM | 1 | 131.34 nM | 0.5% | 4 | 66 nM | 0.5 times | 0.628 | — |
| C-3-3 | 2 | 0.66 nM | 1 | 131.34 nM | 0.5% | 4 | 132 nM | 1 time | 0.443 | — |
| C-3-4 | 2 | 0.66 nM | 1 | 131.34 nM | 0.5% | 4 | 396 nM | 3 times | 0.112 | — |
| C-3-5 | 2 | 0.66 nM | 1 | 131.34 nM | 0.5% | 4 | 660 nM | 5 times | 0.259 | — |
| C-3-6 | 2 | 0.66 nM | 1 | 131.34 nM | 0.5% | 4 | 1320 nM | 10 times | 0.393 | — |

TABLE 4-2

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Equivalent of blocking nucleic acid to nucleic acid mixture | Fluorescence intensity ratio Nucleic acid probe 2 | Nucleic acid probe 3 |
|---|---|---|---|---|---|---|---|---|---|---|
| C-4-1 | 3 | 0.66 nM | 1 | 0.66 nM | 50% | 4 | 0 nM | 0 time | — | 1.091 |
| C-4-2 | 3 | 0.66 nM | 1 | 0.66 nM | 50% | 4 | 0.66 nM | 0.5 times | — | 1.011 |
| C-4-3 | 3 | 0.66 nM | 1 | 0.66 nM | 50% | 4 | 1.32 nM | 1 time | — | 0.811 |
| C-4-4 | 3 | 0.66 nM | 1 | 0.66 nM | 50% | 4 | 3.96 nM | 3 times | — | 0.979 |
| C-4-5 | 3 | 0.66 nM | 1 | 0.66 nM | 50% | 4 | 6.6 nM | 5 times | — | 0.755 |
| C-4-6 | 3 | 0.66 nM | 1 | 0.66 nM | 50% | 4 | 13.2 nM | 10 times | — | 0.000 |
| C-5-1 | 3 | 0.66 nM | 1 | 5.94 nM | 10% | 4 | 0 nM | 0 time | — | 0.746 |
| C-5-2 | 3 | 0.66 nM | 1 | 5.94 nM | 10% | 4 | 3.3 nM | 0.5 times | — | 0.607 |
| C-5-3 | 3 | 0.66 nM | 1 | 5.94 nM | 10% | 4 | 6.6 nM | 1 time | — | 0.633 |
| C-5-4 | 3 | 0.66 nM | 1 | 5.94 nM | 10% | 4 | 19.8 nM | 3 times | — | 0.000 |
| C-5-5 | 3 | 0.66 nM | 1 | 5.94 nM | 10% | 4 | 33 nM | 5 times | — | 0.000 |
| C-5-6 | 3 | 0.66 nM | 1 | 5.94 nM | 10% | 4 | 66 nM | 10 times | — | 0.000 |
| C-6-1 | 3 | 0.66 nM | 1 | 131.34 nM | 0.5% | 4 | 0 nM | 0 time | — | 0.000 |
| C-6-2 | 3 | 0.66 nM | 1 | 131.34 nM | 0.5% | 4 | 66 nM | 0.5 times | — | 0.732 |
| C-6-3 | 3 | 0.66 nM | 1 | 131.34 nM | 0.5% | 4 | 132 nM | 1 time | — | 0.734 |
| C-6-4 | 3 | 0.66 nM | 1 | 131.34 nM | 0.5% | 4 | 396 nM | 3 times | — | 0.253 |
| C-6-5 | 3 | 0.66 nM | 1 | 131.34 nM | 0.5% | 4 | 660 nM | 5 times | — | 0.289 |
| C-6-6 | 3 | 0.66 nM | 1 | 131.34 nM | 0.5% | 4 | 1320 nM | 10 times | — | 0.387 |

TABLE 4-3

| Test conditions | Mutant oligo DNA SEQ ID NO: | Mutant oligo DNA Concentration | Wild-type oligo DNA SEQ ID NO: | Wild-type oligo DNA Concentration | Mutation percentage | Blocking nucleic acid SEQ ID NO: | Blocking nucleic acid Concentration | Equivalent of blocking nucleic acid to nucleic acid mixture | Fluorescence intensity ratio Nucleic acid probe 2 | Fluorescence intensity ratio Nucleic acid probe 3 |
|---|---|---|---|---|---|---|---|---|---|---|
| D-1-1 | — | 0 nM | 1 | 1.32 nM | 0% | 4 | 0 nM | 0 time | 0.373 | 0.732 |
| D-1-2 | — | 0 nM | 1 | 1.32 nM | 0% | 4 | 0.66 nM | 0.5 times | 0.153 | 0.461 |
| D-1-3 | — | 0 nM | 1 | 1.32 nM | 0% | 4 | 1.32 nM | 1 time | 0.097 | 0.429 |
| D-1-4 | — | 0 nM | 1 | 1.32 nM | 0% | 4 | 3.96 nM | 3 times | 0.148 | 0.496 |
| D-1-5 | — | 0 nM | 1 | 1.32 nM | 0% | 4 | 6.6 nM | 5 times | 0.099 | 0.476 |
| D-1-6 | — | 0 nM | 1 | 1.32 nM | 0% | 4 | 13.2 nM | 10 times | 0.000 | 0.000 |
| D-2-1 | — | 0 nM | 1 | 6.6 nM | 0% | 4 | 0 nM | 0 time | 0.267 | 0.765 |
| D-2-2 | — | 0 nM | 1 | 6.6 nM | 0% | 4 | 3.3 nM | 0.5 times | 0.216 | 0.593 |
| D-2-3 | — | 0 nM | 1 | 6.6 nM | 0% | 4 | 6.6 nM | 1 time | 0.188 | 0.500 |
| D-2-4 | — | 0 nM | 1 | 6.6 nM | 0% | 4 | 19.8 nM | 3 times | 0.000 | 0.000 |
| D-2-5 | — | 0 nM | 1 | 6.6 nM | 0% | 4 | 33 nM | 5 times | 0.000 | 0.000 |
| D-2-6 | — | 0 nM | 1 | 6.6 nM | 0% | 4 | 66 nM | 10 times | 0.000 | 0.000 |
| D-3-1 | — | 0 nM | 1 | 132 nM | 0% | 4 | 0 nM | 0 time | 0.000 | 0.000 |
| D-3-2 | — | 0 nM | 1 | 132 nM | 0% | 4 | 66 nM | 0.5 times | 0.000 | 0.000 |
| D-3-3 | — | 0 nM | 1 | 132 nM | 0% | 4 | 132 nM | 1 time | 0.306 | 0.318 |
| D-3-4 | — | 0 nM | 1 | 132 nM | 0% | 4 | 396 nM | 3 times | 0.146 | 0.311 |
| D-3-5 | — | 0 nM | 1 | 132 nM | 0% | 4 | 660 nM | 5 times | 0.235 | 0.346 |
| D-3-6 | — | 0 nM | 1 | 132 nM | 0% | 4 | 1320 nM | 10 times | 0.336 | 0.367 |

In the present Example 2, a difference in the fluorescence intensity ratio was calculated for each exposure time, as with Example 1, and the largest values are shown in Table 5-1, Table 5-2, and FIG. 2.

Using the obtained fluorescence intensity and the measurement results of FIG. 2, a mutation judgment was carried out using a DNA chip, and the mutation judgments [1], [2] and [3] were carried out in the same manner as that of Example 1. The judgment results are shown in Table 5-1 and Table 5-2. It is to be noted that, for example, the term "CD-1-1" in the column "Test conditions" in FIG. 2, Table 5-1 and Table 5-2 is based on the test results obtained under the test conditions "C-1-1" shown in Table 4-1 and the test results obtained under the test conditions "D-1-1" shown in Table 4-3.

TABLE 5-1

| Test condition | Difference in fluorescence intensity ratio | Judgment result [1] | Judgment result [2] | Judgment result [3] |
|---|---|---|---|---|
| CD-1-1 | 0.382 | X | ○ | — |
| CD-1-2 | 0.431 | X | ○ | ○ |
| CD-1-3 | 0.489 | X | ○ | ○ |
| CD-1-4 | 0.443 | X | ○ | ○ |
| CD-1-5 | 0.437 | X | ○ | ○ |
| CD-1-6 | 0.000 | X | X | X |
| CD-2-1 | 0.165 | X | ○ | — |
| CD-2-2 | 0.086 | X | X | X |
| CD-2-3 | 0.113 | X | ○ | ○ |
| CD-2-4 | 0.000 | X | X | X |
| CD-2-5 | 0.000 | X | X | X |
| CD-2-6 | 0.000 | X | X | X |
| CD-3-1 | 0.000 | X | X | — |
| CD-3-2 | 0.000 | X | X | X |
| CD-3-3 | 0.122 | X | ○ | ○ |
| CD-3-4 | 0.000 | X | X | X |
| CD-3-5 | 0.023 | X | X | X |
| CD-3-6 | 0.057 | X | X | X |

TABLE 5-2

| Test condition | Difference in fluorescence intensity ratio | Judgment result [1] | Judgment result [2] | Judgment result [3] |
|---|---|---|---|---|
| CD-4-1 | 0.373 | ○ | ○ | — |
| CD-4-2 | 0.550 | ○ | ○ | ○ |
| CD-4-3 | 0.397 | X | ○ | ○ |
| CD-4-4 | 0.528 | X | ○ | ○ |
| CD-4-5 | 0.283 | X | ○ | ○ |
| CD-4-6 | 0.000 | X | X | X |
| CD-5-1 | 0.001 | X | X | — |
| CD-5-2 | 0.014 | X | X | X |
| CD-5-3 | 0.149 | X | ○ | ○ |
| CD-5-4 | 0.000 | X | X | X |
| CD-5-5 | 0.000 | X | X | X |
| CD-5-6 | 0.000 | X | X | X |
| CD-6-1 | 0.000 | X | X | — |
| CD-6-2 | 0.000 | X | X | X |
| CD-6-3 | 0.416 | X | ○ | ○ |
| CD-6-4 | 0.000 | X | X | X |
| CD-6-5 | 0.000 | X | X | X |
| CD-6-6 | 0.020 | X | X | X |

As shown in Table 5-1 and Table 5-2, in the present Example 2, regarding the mutation judgment [1], there were no conditions corresponding to a positive judgment. However, regarding the mutation judgment [2], it became clear that a mutation judgment can be performed with a blocking nucleic acid at 0 to 5 times, if the mutation percentage is 50%, and that the mutation judgment can be performed only in the case of using a blocking nucleic acid at 1 time, if the mutation percentage is 10% and 0.5%. Moreover, regarding the mutation judgment [3], it became clear that a mutation judgment can be performed with a blocking nucleic acid at 0.5 to 5 times, if the mutation percentage is 50%, and that the mutation judgment can be performed only in the case of using a blocking nucleic acid at 1 time, if the mutation percentage is 10% and 0.5%.

From the aforementioned results, it has been revealed that a favorable mutation judgment can be carried out in a nucleic acid mixture comprising 0.66 nM mutant oligo DNA at a mutation percentage of 0.5% to 10%, by adding a blocking nucleic acid at 1 time to the nucleic acid mixture.

Example 3

In the present example, the wild-type nucleotide sequence (GGT) of Codon 12 in K-ras was determined to be non-detection target nucleotides, and mutant nucleotide sequences (GAT, GTT, and GCT) were determined to be detection target nucleotides. As a wild-type specimen, oligo DNA consisting of 26 nucleotides having the wild-type nucleotide sequence (GGT) of Codon 12 in the center thereof (wild-type oligo DNA 2) was used. As mutant specimens, oligo DNAs each consisting of 24 nucleotides having the mutant nucleotide sequence (GAT, GTT, or GCT) of Codon 12 in the center thereof (mutant oligo DNAs 3 to 5) were used. The wild-type oligo DNA 2 and the mutant oligo DNAs 3 to 5 each had a 5'-terminus labeled with Cyanine5 (Cy5). The concentration of the mutant oligo DNA was set at 0.66 nM, and the wild-type oligo DNA was mixed with the mutant oligo DNAs to result in a mutation percentage of 0.5%, 1% or 5%, thereby preparing a nucleic acid mixture.

In the present example, non-detection target nucleotides, namely, a blocking nucleic acid 2 complementary to the wild-type nucleotide sequence (GGT) was designed (sequence: GAGCTggtGGCGTA; SEQ ID NO: 12). A buffer composition for hybridization comprising the blocking nucleic acid was mixed with the above-obtained nucleic acid mixture to prepare a hybridization reaction solution (containing 1×SSC/0.1% SDS).

The hybridization reaction solution was added dropwise onto a DNA chip, and a hybridization cover was applied thereon, followed by performing a reaction at 45° C. for 1 hour in a hybridization chamber. As such a DNA chip, GENE SILICON® (manufactured by Toyo Kohan Co., Ltd.) was used. Besides, this DNA chip comprises a nucleic acid probe 4 (GAGCTggtGGCGTA (SEQ ID NO: 13)) for detecting the wild-type oligo DNA 2, a nucleic acid probe 5 (GAGCTgatGGCGTAG (SEQ ID NO: 14)) for detecting the mutant oligo DNA 3, a nucleic acid probe 6 (AGCTgttGGCGTAG (SEQ ID NO: 15)) for detecting the mutant oligo DNA 4, and a nucleic acid probe 7 (GCTgctGGCGTAG (SEQ ID NO: 16)) for detecting the mutant oligo DNA 5.

The nucleotide sequences of the wild-type oligo DNA 2, the mutant oligo DNAs 3 to 5, the blocking nucleic acid 2, and the nucleic acid probes 4 to 7 are collectively shown in Table 6.

TABLE 6

| Name | SEQ ID NO: | Sequence (5' to 3') | Number of nucleotides |
|---|---|---|---|
| Wild-type oligo DNA 2 | 8 | Cy5-CTTGCCTACGCC ACCAGCTCCAACTA | 26 |
| Mutant oligo DNA 3 | 9 | Cy5-CTTGCCTACGCC ATCAGCTCCAAC | 24 |
| Mutant oligo DNA 4 | 10 | Cy5-CTTGCCTACGCC AACAGCTCCAAC | 24 |
| Mutant oligo DNA 5 | 11 | Cy5-CTTGCCTACGCC AGCAGCTCCAAC | 24 |
| Blocking nucleic acid 2 | 12 | GAGCTGGTGGCGTA | 14 |
| Nucleic acid probe 4 | 13 | GAGCTGGTGGCGTA | 14 |
| Nucleic acid probe 5 | 14 | GAGCTGATGGCGTAG | 15 |
| Nucleic acid probe 6 | 15 | AGCTGTTGGCGTAG | 14 |
| Nucleic acid probe 7 | 16 | GCTGCTGGCGTAG | 13 |

The composition ratio between mutant oligo DNA and wild-type oligo DNA comprised in a nucleic acid mixture, the concentration of a blocking nucleic acid, and the equivalent amount of a blocking nucleic acid, in each experimental plot, are collectively shown in Table 7-1 to Table 7-4.

TABLE 7-1

| Test conditions | Mutant oligo DNA SEQ ID NO: | Mutant oligo DNA Concentration | Wild-type oligo DNA SEQ ID NO: | Wild-type oligo DNA Concentration | Mutation percentage | Blocking nucleic acid SEQ ID NO: | Blocking nucleic acid Concentration | Equivalent of blocking nucleic acid to nucleic acid mixture | Fluorescence intensity ratio Nucleic acid probe 5 | Fluorescence intensity ratio Nucleic acid probe 6 | Fluorescence intensity ratio Nucleic acid probe 7 |
|---|---|---|---|---|---|---|---|---|---|---|---|
| E-1-1 | 9 | 0.66 nM | 8 | 12.54 nM | 5% | 12 | 0 nM | 0 time | 1.917 | — | — |
| E-1-2 | 9 | 0.66 nM | 8 | 12.54 nM | 5% | 12 | 6.6 nM | 0.5 times | 1.883 | — | — |
| E-1-3 | 9 | 0.66 nM | 8 | 12.54 nM | 5% | 12 | 13.2 nM | 1 time | 2.388 | — | — |
| E-1-4 | 9 | 0.66 nM | 8 | 12.54 nM | 5% | 12 | 39.6 nM | 3 times | 3.330 | — | — |
| E-1-5 | 9 | 0.66 nM | 8 | 12.54 nM | 5% | 12 | 66 nM | 5 times | 2.526 | — | — |
| E-1-6 | 9 | 0.66 nM | 8 | 12.54 nM | 5% | 12 | 132 nM | 10 times | 3.590 | — | — |
| E-2-1 | 9 | 0.66 nM | 8 | 65.34 nM | 1% | 12 | 0 nM | 0 time | 1.134 | — | — |
| E-2-2 | 9 | 0.66 nM | 8 | 65.34 nM | 1% | 12 | 33 nM | 0.5 times | 0.895 | — | — |
| E-2-3 | 9 | 0.66 nM | 8 | 65.34 nM | 1% | 12 | 66 nM | 1 time | 3.204 | — | — |
| E-2-4 | 9 | 0.66 nM | 8 | 65.34 nM | 1% | 12 | 198 nM | 3 times | 4.586 | — | — |
| E-2-5 | 9 | 0.66 nM | 8 | 65.34 nM | 1% | 12 | 330 nM | 5 times | 3.001 | — | — |
| E-2-6 | 9 | 0.66 nM | 8 | 65.34 nM | 1% | 12 | 660 nM | 10 times | 6.049 | — | — |
| E-3-1 | 9 | 0.66 nM | 8 | 131.34 nM | 0.5% | 12 | 0 nM | 0 time | 2.382 | — | — |

TABLE 7-1-continued

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Equivalent of blocking nucleic acid to nucleic acid mixture | Fluorescence intensity ratio Nucleic acid probe 5 | Nucleic acid probe 6 | Nucleic acid probe 7 |
|---|---|---|---|---|---|---|---|---|---|---|---|
| E-3-2 | 9 | 0.66 nM | 8 | 131.34 nM | 0.5% | 12 | 66 nM | 0.5 times | 1.203 | — | — |
| E-3-3 | 9 | 0.66 nM | 8 | 131.34 nM | 0.5% | 12 | 132 nM | 1 time | 1.987 | — | — |
| E-3-4 | 9 | 0.66 nM | 8 | 131.34 nM | 0.5% | 12 | 396 nM | 3 times | 3.591 | — | — |
| E-3-5 | 9 | 0.66 nM | 8 | 131.34 nM | 0.5% | 12 | 660 nM | 5 times | 4.830 | — | — |
| E-3-6 | 9 | 0.66 nM | 8 | 131.34 nM | 0.5% | 12 | 1320 nM | 10 times | 8.065 | — | — |

TABLE 7-2

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Equivalent of blocking nucleic acid to nucleic acid mixture | Fluorescence intensity ratio Nucleic acid probe 5 | Nucleic acid probe 6 | Nucleic acid probe 7 |
|---|---|---|---|---|---|---|---|---|---|---|---|
| E-4-1 | 10 | 0.66 nM | 8 | 12.54 nM | 5% | 12 | 0 nM | 0 time | — | 0.927 | — |
| E-4-2 | 10 | 0.66 nM | 8 | 12.54 nM | 5% | 12 | 6.6 nM | 0.5 times | — | 1.286 | — |
| E-4-3 | 10 | 0.66 nM | 8 | 12.54 nM | 5% | 12 | 13.2 nM | 1 time | — | 1.446 | — |
| E-4-4 | 10 | 0.66 nM | 8 | 12.54 nM | 5% | 12 | 39.6 nM | 3 times | — | 1.436 | — |
| E-4-5 | 10 | 0.66 nM | 8 | 12.54 nM | 5% | 12 | 66 nM | 5 times | — | 1.711 | — |
| E-4-6 | 10 | 0.66 nM | 8 | 12.54 nM | 5% | 12 | 132 nM | 10 times | — | 1.861 | — |
| E-5-1 | 10 | 0.66 nM | 8 | 65.34 nM | 1% | 12 | 0 nM | 0 time | — | 1.098 | — |
| E-5-2 | 10 | 0.66 nM | 8 | 65.34 nM | 1% | 12 | 33 nM | 0.5 times | — | 0.939 | — |
| E-5-3 | 10 | 0.66 nM | 8 | 65.34 nM | 1% | 12 | 66 nM | 1 time | — | 1.075 | — |
| E-5-4 | 10 | 0.66 nM | 8 | 65.34 nM | 1% | 12 | 198 nM | 3 times | — | 1.736 | — |
| E-5-5 | 10 | 0.66 nM | 8 | 65.34 nM | 1% | 12 | 330 nM | 5 times | — | 2.895 | — |
| E-5-6 | 10 | 0.66 nM | 8 | 65.34 nM | 1% | 12 | 660 nM | 10 times | — | 3.518 | — |
| E-6-1 | 10 | 0.66 nM | 8 | 131.34 nM | 0.5% | 12 | 0 nM | 0 time | — | 1.090 | — |
| E-6-2 | 10 | 0.66 nM | 8 | 131.34 nM | 0.5% | 12 | 66 nM | 0.5 times | — | 1.006 | — |
| E-6-3 | 10 | 0.66 nM | 8 | 131.34 nM | 0.5% | 12 | 132 nM | 1 time | — | 1.044 | — |
| E-6-4 | 10 | 0.66 nM | 8 | 131.34 nM | 0.5% | 12 | 396 nM | 3 times | — | 2.488 | — |
| E-6-5 | 10 | 0.66 nM | 8 | 131.34 nM | 0.5% | 12 | 660 nM | 5 times | — | 2.691 | — |
| E-6-6 | 10 | 0.66 nM | 8 | 131.34 nM | 0.5% | 12 | 1320 nM | 10 times | — | 3.923 | — |

TABLE 7-3

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Equivalent of blocking nucleic acid to nucleic acid mixture | Fluorescence intensity ratio Nucleic acid probe 5 | Nucleic acid probe 6 | Nucleic acid probe 7 |
|---|---|---|---|---|---|---|---|---|---|---|---|
| E-7-1 | 11 | 0.66 nM | 8 | 12.54 nM | 5% | 12 | 0 nM | 0 time | — | — | 1.409 |
| E-7-2 | 11 | 0.66 nM | 8 | 12.54 nM | 5% | 12 | 6.6 nM | 0.5 times | — | — | 1.700 |
| E-7-3 | 11 | 0.66 nM | 8 | 12.54 nM | 5% | 12 | 13.2 nM | 1 time | — | — | 1.850 |
| E-7-4 | 11 | 0.66 nM | 8 | 12.54 nM | 5% | 12 | 39.6 nM | 3 times | — | — | 2.113 |
| E-7-5 | 11 | 0.66 nM | 8 | 12.54 nM | 5% | 12 | 66 nM | 5 times | — | — | 2.054 |
| E-7-6 | 11 | 0.66 nM | 8 | 12.54 nM | 5% | 12 | 132 nM | 10 times | — | — | 2.210 |
| E-8-1 | 11 | 0.66 nM | 8 | 65.34 nM | 1% | 12 | 0 nM | 0 time | — | — | 1.190 |
| E-8-2 | 11 | 0.66 nM | 8 | 65.34 nM | 1% | 12 | 33 nM | 0.5 times | — | — | 0.968 |
| E-8-3 | 11 | 0.66 nM | 8 | 65.34 nM | 1% | 12 | 66 nM | 1 time | — | — | 2.503 |
| E-8-4 | 11 | 0.66 nM | 8 | 65.34 nM | 1% | 12 | 198 nM | 3 times | — | — | 2.014 |
| E-8-5 | 11 | 0.66 nM | 8 | 65.34 nM | 1% | 12 | 330 nM | 5 times | — | — | 3.019 |
| E-8-6 | 11 | 0.66 nM | 8 | 65.34 nM | 1% | 12 | 660 nM | 10 times | — | — | 4.586 |

TABLE 7-3-continued

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Equivalent of blocking nucleic acid to nucleic acid mixture | Fluorescence intensity ratio Nucleic acid probe 5 | Nucleic acid probe 6 | Nucleic acid probe 7 |
|---|---|---|---|---|---|---|---|---|---|---|---|
| E-9-1 | 11 | 0.66 nM | 8 | 131.34 nM | 0.5% | 12 | 0 nM | 0 time | — | — | 2.732 |
| E-9-2 | 11 | 0.66 nM | 8 | 131.34 nM | 0.5% | 12 | 66 nM | 0.5 times | — | — | 2.031 |
| E-9-3 | 11 | 0.66 nM | 8 | 131.34 nM | 0.5% | 12 | 132 nM | 1 time | — | — | 1.394 |
| E-9-4 | 11 | 0.66 nM | 8 | 131.34 nM | 0.5% | 12 | 396 nM | 3 times | — | — | 3.440 |
| E-9-5 | 11 | 0.66 nM | 8 | 131.34 nM | 0.5% | 12 | 660 nM | 5 times | — | — | 4.300 |
| E-9-6 | 11 | 0.66 nM | 8 | 131.34 nM | 0.5% | 12 | 1320 nM | 10 times | — | — | 6.622 |

TABLE 7-4

| Test conditions | Mutant oligo DNA SEQ ID NO: | Concentration | Wild-type oligo DNA SEQ ID NO: | Concentration | Mutation percentage | Blocking nucleic acid SEQ ID NO: | Concentration | Equivalent of blocking nucleic acid to nucleic acid mixture | Fluorescence intensity ratio Nucleic acid probe 5 | Nucleic acid probe 6 | Nucleic acid probe 7 |
|---|---|---|---|---|---|---|---|---|---|---|---|
| F-1-1 | — | 0 nM | 8 | 13.2 nM | 0% | 12 | 0 nM | 0 time | 0.300 | 0.051 | 0.009 |
| F-1-2 | — | 0 nM | 8 | 13.2 nM | 0% | 12 | 6.6 nM | 0.5 times | 0.316 | 0.049 | 0.008 |
| F-1-3 | — | 0 nM | 8 | 13.2 nM | 0% | 12 | 132 nM | 1 time | 0.116 | 0.008 | 0.000 |
| F-1-4 | — | 0 nM | 8 | 13.2 nM | 0% | 12 | 39.6 nM | 3 times | 0.067 | 0.000 | 0.000 |
| F-1-5 | — | 0 nM | 8 | 13.2 nM | 0% | 12 | 66 nM | 5 times | 0.078 | 0.002 | 0.000 |
| F-1-6 | — | 0 nM | 8 | 13.2 nM | 0% | 12 | 132 nM | 10 times | 0.088 | 0.000 | 0.000 |
| F-2-1 | — | 0 nM | 8 | 66 nM | 0% | 12 | 0 nM | 0 time | 0.464 | 0.108 | 0.022 |
| F-2-2 | — | 0 nM | 8 | 66 nM | 0% | 12 | 33 nM | 0.5 times | 0.557 | 0.081 | 0.018 |
| F-2-3 | — | 0 nM | 8 | 66 nM | 0% | 12 | 66 nM | 1 time | 0.202 | 0.011 | 0.008 |
| F-2-4 | — | 0 nM | 8 | 66 nM | 0% | 12 | 198 nM | 3 times | 4.586 | 0.299 | 0.240 |
| F-2-5 | — | 0 nM | 8 | 66 nM | 0% | 12 | 330 nM | 5 times | 0.134 | 0.000 | 0.000 |
| F-2-6 | — | 0 nM | 8 | 66 nM | 0% | 12 | 660 nM | 10 times | 0.142 | 0.009 | 0.003 |
| F-3-1 | — | 0 nM | 8 | 132 nM | 0% | 12 | 0 nM | 0 time | 0.893 | 0.263 | 0.083 |
| F-3-2 | — | 0 nM | 8 | 132 nM | 0% | 12 | 66 nM | 0.5 times | 0.518 | 0.117 | 0.033 |
| F-3-3 | — | 0 nM | 8 | 132 nM | 0% | 12 | 132 nM | 1 time | 0.270 | 0.022 | 0.006 |
| F-3-4 | — | 0 nM | 8 | 132 nM | 0% | 12 | 396 nM | 3 times | 0.191 | 0.000 | 0.000 |
| F-3-5 | — | 0 nM | 8 | 132 nM | 0% | 12 | 660 nM | 5 times | 0.188 | 0.000 | 0.000 |
| F-3-6 | — | 0 nM | 8 | 132 nM | 0% | 12 | 1320 nM | 10 times | 0.174 | 0.000 | 0.000 |

In the present Example 3, a difference in the fluorescence intensity ratio was obtained for each exposure time, and the largest values are shown in Table 8-1, Table 8-2, Table 8-3 and FIG. 3.

Using the obtained fluorescence intensity and the measurement results shown in FIG. 3, a mutation judgment was carried out using a DNA chip, and the mutation judgments [1], [2] and [3] were carried out in the same manner as that of Example 1. The obtained judgment results are shown in Table 8-1 to Table 8-3. It is to be noted that, for example, the term "EF-1-1" in the column "Test conditions" in FIG. 3, and Table 8-1 to Table 8-3 is based on the test results obtained under the test conditions "E-1-1" shown in Table 7-1 and the test results obtained under the test conditions "F-1-1" shown in Table 7-4.

TABLE 8-1

| Test condition | Difference in fluorescence intensity ratio | Judgment result [1] | Judgment result [2] | Judgment result [3] |
|---|---|---|---|---|
| EF-1-1 | 1.620 | ○ | ○ | — |
| EF-1-2 | 1.567 | ○ | ○ | X |
| EF-1-3 | 2.275 | ○ | ○ | ○ |
| EF-1-4 | 3.265 | ○ | ○ | ○ |
| EF-1-5 | 2.448 | ○ | ○ | ○ |
| EF-1-6 | 3.275 | ○ | ○ | ○ |
| EF-2-1 | 0.670 | ○ | ○ | — |
| EF-2-2 | 0.337 | X | ○ | ○ |
| EF-2-3 | 3.003 | ○ | ○ | ○ |
| EF-2-4 | 0.000 | X | X | X |

TABLE 8-1-continued

| Test condition | Difference in fluorescence intensity ratio | Judgment result [1] | Judgment result [2] | Judgment result [3] |
|---|---|---|---|---|
| EF-2-5 | 2.867 | ○ | ○ | ○ |
| EF-2-6 | 5.726 | ○ | ○ | ○ |
| EF-3-1 | 1.488 | ○ | ○ | — |
| EF-3-2 | 0.634 | ○ | ○ | X |
| EF-3-3 | 1.717 | ○ | ○ | ○ |
| EF-3-4 | 3.405 | ○ | ○ | ○ |
| EF-3-5 | 4.652 | ○ | ○ | ○ |
| EF-3-6 | 7.908 | ○ | ○ | ○ |

TABLE 8-2

| Test condition | Difference in fluorescence intensity ratio | Judgment result [1] | Judgment result [2] | Judgment result [3] |
|---|---|---|---|---|
| EF-4-1 | 0.875 | X | ○ | — |
| EF-4-2 | 1.237 | ○ | ○ | ○ |
| EF-4-3 | 1.438 | ○ | ○ | ○ |
| EF-4-4 | 1.438 | ○ | ○ | ○ |
| EF-4-5 | 1.715 | ○ | ○ | ○ |
| EF-4-6 | 1.812 | ○ | ○ | ○ |
| EF-5-1 | 0.962 | ○ | ○ | — |
| EF-5-2 | 0.858 | X | ○ | ○ |
| EF-5-3 | 1.064 | ○ | ○ | ○ |
| EF-5-4 | 1.448 | ○ | ○ | ○ |
| EF-5-5 | 2.900 | ○ | ○ | ○ |
| EF-5-6 | 3.514 | ○ | ○ | ○ |
| EF-6-1 | 0.835 | ○ | ○ | — |
| EF-6-2 | 0.889 | ○ | ○ | ○ |
| EF-6-3 | 1.023 | ○ | ○ | ○ |
| EF-6-4 | 2.494 | ○ | ○ | ○ |
| EF-6-5 | 2.697 | ○ | ○ | ○ |
| EF-6-6 | 3.961 | ○ | ○ | ○ |

TABLE 8-3

| Test condition | Difference in fluorescence intensity ratio | Judgment result [1] | Judgment result [2] | Judgment result [3] |
|---|---|---|---|---|
| EF-7-1 | 1.399 | ○ | ○ | — |
| EF-7-2 | 1.692 | ○ | ○ | ○ |
| EF-7-3 | 1.850 | ○ | ○ | ○ |
| EF-7-4 | 2.117 | ○ | ○ | ○ |
| EF-7-5 | 2.054 | ○ | ○ | ○ |
| EF-7-6 | 2.208 | ○ | ○ | ○ |
| EF-8-1 | 1.168 | ○ | ○ | — |
| EF-8-2 | 0.950 | X | ○ | ○ |
| EF-8-3 | 2.495 | ○ | ○ | ○ |
| EF-8-4 | 1.781 | ○ | ○ | ○ |
| EF-8-5 | 3.026 | ○ | ○ | ○ |
| EF-8-6 | 4.587 | ○ | ○ | ○ |
| EF-9-1 | 2.649 | ○ | ○ | — |
| EF-9-2 | 1.998 | ○ | ○ | X |
| EF-9-3 | 1.388 | ○ | ○ | X |
| EF-9-4 | 3.456 | ○ | ○ | ○ |
| EF-9-5 | 4.307 | ○ | ○ | ○ |
| EF-9-6 | 6.595 | ○ | ○ | ○ |

As shown in Table 8-1 to Table 8-3, in the present Example 3, regarding the mutation judgment [1], a positive judgment was obtained under almost all conditions in all cases of a mutation percentage of 0.5% to 5%. Moreover, in the mutation judgment [2] as well, in all cases of a mutation percentage of 0.5% to 5%, a positive judgment was obtained under almost all conditions. Furthermore, regarding the mutation judgment [3], in the case of a mutation percentage of 1% to 5%, a positive judgment was obtained under almost all conditions, and in the case of a mutation percentage of 0.5%, it was possible to carry out a mutation judgment at the ratio of mixing a blocking nucleic acid that was 3 times or more.

Table 9 shows the GC percentage of the nucleic acid probe used in the present example, and a difference ($\Delta$Tm) between Tm (w) and Tm (m), wherein Tm (w) between [wild-type oligo DNA–blocking nucleic acid] and Tm (m) between [mutant oligo DNA–blocking nucleic acid] were calculated according to the nearest neighbor method.

TABLE 9

| Name | GC percentage (%) | $\Delta$Tm |
|---|---|---|
| Nucleic acid probe 1 | 29% | — |
| Nucleic acid probe 2 | 32% | 5.51 |
| Nucleic acid probe 3 | 29% | 6.64 |
| Nucleic acid probe 4 | 64% | — |
| Nucleic acid probe 5 | 60% | 8.02 |
| Nucleic acid probe 6 | 57% | 10.69 |
| Nucleic acid probe 7 | 69% | 16.02 |

As is found from Table 9, the GC percentage of the nucleic acid probe of Codon 12 in K-ras was 57% or more, and based on Tm (w) between [wild-type oligo DNA–blocking nucleic acid] and Tm (m) between [mutant oligo DNA–blocking nucleic acid], the difference ($\Delta$Tm) between Tm (w) and Tm (m) was 8° C. or higher. In contrast, the GC percentage of the nucleic acid probe of Codon 117 in K-ras was 32% or less, and thus, the $\Delta$Tm is found to be 6.6° C. or lower. From these results, it can be said that the nucleic acid probe of Codon 12 has been designed under conditions more advantageous for the mutation judgment, than the nucleic acid probe of Codon 117. Therefore, the blocking nucleic acid of the present example is particularly effective, when it is applied in a combination of a target and a probe that is disadvantageous for the mutation judgment, in which the GC percentage is 32% or less, and the $\Delta$Tm is 6.6° C. or lower, and preferably 5.5° C. to 6.6° C. When the blocking nucleic acid is added in a concentration of 1 to 3 times to a nucleic acid mixture comprising 0.66 to 3.3 nM mutant oligo DNA at a mutation percentage of 0.5% to 10%, it becomes possible to carry out a mutation judgment, and addition of the blocking nucleic acid in a concentration of 1 time is more preferable.

All publications, patents, and patent applications cited in the present description are incorporated herein by reference in their entirety.

The invention claimed is:

1. A method of hybridizing a target nucleic acid comprising a detection target nucleotide with a nucleic acid probe comprising a nucleotide sequence complementary to a region comprising at least the detection target nucleotide in the target nucleic acid, wherein the method comprises: mixing a solution comprising a nucleic acid mixture consisting of the target nucleic acid and a non-target nucleic acid comprising a non-detection target nucleotide corresponding to the detection target nucleotide, with a buffer composition for hybridization containing a blocking nucleic acid comprising a nucleotide sequence complementary to a region comprising at least the non-detection target nucleotide in the non-target nucleic acid, in a concentration 1 to 3 times higher than the concentration of both the target and non-target nucleic acids in the nucleic acid mixture; and then hybridizing the nucleic acid probe with the target nucleic acid, wherein the solution comprising the nucleic acid mixture contains the target nucleic acid at a percentage of 0.5% to 10%, when the total percentage of the target nucleic acid and the non-target nucleic acid is set at 100%, and wherein the nucleic acid mixture contains the target nucleic acid in a concentration of 0.66 nM to 3.3 nM.

2. The hybridization method according to claim 1, wherein a mixed solution prepared by mixing the buffer composition for hybridization with the solution comprising the nucleic acid mixture is allowed to come into contact with a microarray formed by immobilizing the nucleic acid probes on a substrate.

3. The hybridization method according to claim 1, wherein the solution comprising the nucleic acid mixture is a reaction solution obtained after completion of a nucleic acid amplification reaction for amplifying the target nucleic acid, and the reaction solution is mixed with the buffer composition for hybridization.

* * * * *